US012398100B2

(12) United States Patent
Rao et al.

(10) Patent No.: US 12,398,100 B2
(45) Date of Patent: Aug. 26, 2025

(54) METHODS AND INTERMEDIATES FOR PREPARING HYDROCHLORIDE SALT OF 5-[3-(3-HYDROXYPHENOXY)AZETIDIN-1-YL]-5-METHYL-2,2-DIPHENYLHEXANAMIDE

(71) Applicants: MYLAN LABORATORIES LIMITED, Hyderabad (IN); PFIZER LIMITED, Kent (GB)

(72) Inventors: Vadali Lakshmana Rao, Hyderabad (IN); Saidugari Swamy, Hyderabad (IN); Nagaraju Mittapelly, Hyderabad (IN); Dasari Srinivasa Rao, Hyderabad (IN); Sarah Haycock Lewandowski, Kent (GB); Alan Pettman, Kent (GB)

(73) Assignees: Mylan Laboratories Limited, Hyderabad (IN); Pfizer Limited, Kent (GB)

( * ) Notice: Subject to any disclaimer, the term of this patent is extended or adjusted under 35 U.S.C. 154(b) by 912 days.

(21) Appl. No.: 17/622,605

(22) PCT Filed: Jun. 24, 2020

(86) PCT No.: PCT/IB2020/055996
§ 371 (c)(1),
(2) Date: Dec. 23, 2021

(87) PCT Pub. No.: WO2020/261160
PCT Pub. Date: Dec. 30, 2020

(65) Prior Publication Data
US 2022/0380307 A1 Dec. 1, 2022

Related U.S. Application Data

(60) Provisional application No. 62/866,174, filed on Jun. 25, 2019.

(51) Int. Cl.
*C07D 205/04* (2006.01)
(52) U.S. Cl.
CPC ................... *C07D 205/04* (2013.01)
(58) Field of Classification Search
CPC .................................................... C07D 205/04
See application file for complete search history.

(56) References Cited

U.S. PATENT DOCUMENTS

2010/0113409 A1  5/2010  Glossop et al.
2011/0251164 A1  10/2011  Glossop et al.

OTHER PUBLICATIONS

Glossop, 2011, J Med Chem, vol. 54, 6888-6914. (Year: 2011).*
Dillon et al. "Synthesis of PF-3635659", Synfacts. 2012. vol. 8(5), p. 467, entire document.
Glossop et al. "Inhalation by Design: Novel Tertiary Amine Muscarinic M3 Receptor Antagonists with Slow Off-Rate Binding Kinetics for Inhaled Once-Daily Treatment of Chronic Obstructive Pulmonary Disease", J. Med. Chem. 2011. vol. 54, pp. 6888-6904, entire document.
International Search Report and Written Opinion of the International Searching Authority (ISA/US) mailed Oct. 19, 2020 in International PCT Application No. PCT/IB2020/055996 filed Jun. 24, 2020.

* cited by examiner

*Primary Examiner* — D Margaret M Seaman
(74) *Attorney, Agent, or Firm* — Sorell, Lenna & Schmidt, LLP

(57) ABSTRACT

Methods for providing a carboxamide compound and intermediates used in the preparation of the carboxamide compound are provided. The methods include reacting 5-[3-(3-hydroxyphenoxy)azetidin-1-yl]-5-methyl-2,2-diphenylhexanenitrile benzoate with a reagent and hydrochloric acid to form the carboxamide compound including 5-[3-(3-hydroxyphenoxy)azetidin-1-yl]-5-methyl-2,2-diphenylhexanamide hydrochloride.

17 Claims, 3 Drawing Sheets

METHODS AND INTERMEDIATES FOR PREPARING HYDROCHLORIDE SALT OF 5-[3-(3-HYDROXYPHENOXY)AZETIDIN-1-YL]-5-METHYL-2,2-DIPHENYLHEXANAMIDE

CROSS REFERENCE TO RELATED APPLICATION(S)

The present application claims priority to U.S. Provisional Patent Application No. 62/866,174, filed on Jun. 25, 2019, which is incorporated herein by reference in its entirety.

BACKGROUND

Field

Cholinergic muscarinic receptors are members of the G-protein coupled receptor super-family and are further divided into 5 subtypes, $M_1$ to $M_5$. Muscarinic receptor sub-types are widely and differentially expressed in the body. Genes have been cloned for all 5 sub-types and of these, $M_1$, $M_2$, and $M_3$ receptors have been extensively pharmacologically characterized in animal and human tissue. $M_1$ receptors are expressed in the brain (cortex and hippocampus), glands and in the ganglia of sympathetic and parasympathetic nerves. $M_2$ receptors are expressed in the heart, hindbrain, smooth muscle and in the synapses of the autonomic nervous system. $M_3$ receptors are expressed in the brain, glands and smooth muscle. In the airways, stimulation of $M_3$ receptors evokes contraction of airway smooth muscle leading to bronchoconstriction, while in the salivary gland $M_3$ receptor stimulation increases fluid and mucus secretion leading to increased salivation. $M_2$ receptors expressed on smooth muscle are understood to be pro-contractile while pre-synaptic $M_2$ receptors modulate acetylcholine release from parasympathetic nerves. Stimulation of $M_2$ receptors expressed in the heart produces bradycardia.

Short and long-acting muscarinic antagonists are used in the management of asthma and chronic obstructive pulmonary disease (COPD); these include the short acting agents Atrovent® (ipratropium bromide) and Oxivent® (oxitropium bromide) and the long acting agent Spiriva® (tiotropium bromide). These compounds produce bronchodilation following inhaled administration. In addition to improvements in spirometric values, anti-muscarinic use in COPD is associated with improvements in health status and quality of life scores. As a consequence of the wide distribution of muscarinic receptors in the body, significant systemic exposure to muscarinic antagonists is associated with effects such as dry mouth, constipation, mydriasis, urinary retention (all predominantly mediated via blockade of $M_3$ receptors) and tachycardia (mediated by blockade of $M_2$ receptors).

A newer $M_3$ receptor antagonist that is in the carboxamide family is 5-[3-(3-hydroxyphenoxy)azetidin-1-yl]-5-methyl-2,2-diphenylhexanamide hydrochloride. This carboxamide compound exhibits the following structure (formula II):

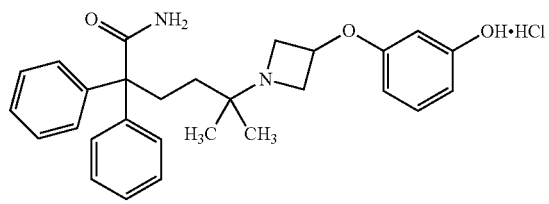

To date, it has not been appreciated that 5-[3-(3-hydroxyphenoxy)azetidin-1-yl]-5-methyl-2,2-diphenylhexanamide hydrochloride can be synthesized from the benzoate salt of 5-[3-(3-hydroxyphenoxy)azetidin-1-yl]-5-methyl-2,2-diphenylhexanenitrile. Therefore, there is a need for methods and intermediates used to efficiently prepare 5-[3-(3-hydroxyphenoxy)azetidin-1-yl]-5-methyl-2,2-diphenylhexanamide hydrochloride of good quality from the benzoate salt of 5-[3-(3-hydroxyphenoxy)azetidin-1-yl]-5-methyl-2,2-diphenylhexanenitrile.

SUMMARY

Methods for providing a carboxamide compound and intermediates used in the preparation of the carboxamide compound are provided. In some embodiments, methods and intermediates are provided that are used to prepare 5-[3-(3-hydroxyphenoxy)azetidin-1-yl]-5-methyl-2,2-diphenylhexanamide hydrochloride from a benzoate salt.

The methods described in this application include reacting 5-[3-(3-hydroxyphenoxy)azetidin-1-yl]-5-methyl-2,2-diphenylhexanenitrile benzoate with a reagent and hydrochloric acid to form the carboxamide compound 5-[3-(3-hydroxyphenoxy)azetidin-1-yl]-5-methyl-2,2-diphenylhexanamide hydrochloride.

In some non-limiting embodiments, the methods of preparing a carboxamide of formula II

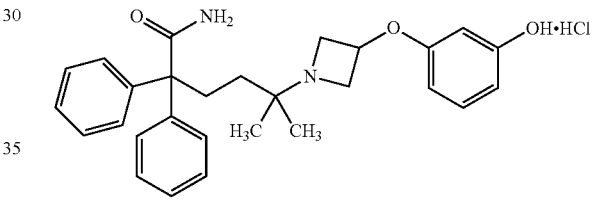

include reacting 5-[3-(3-hydroxyphenoxy)azetidin-1-yl]-5-methyl-2,2-diphenyl-hexanenitrile benzoate of formula I

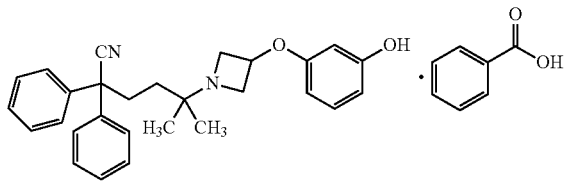 [SMILES: CC(C)(CCC(C#N)(c1ccccc1)c1ccccc1)N1CC(Oc2cccc(O)c2)C1 ; O=C(O)c1ccccc1]

with a reagent and hydrochloric acid to form the carboxamide compound comprising 5-[3-(3-hydroxyphenoxy)azetidin-1-yl]-5-methyl-2,2-diphenylhexanamide hydrochloride of formula II

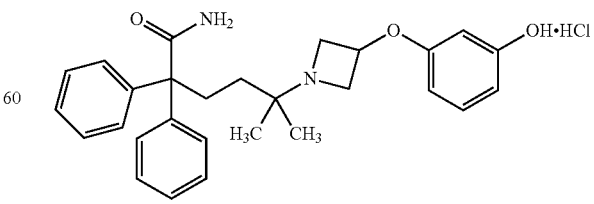

Intermediates formed in the preparation of the carboxamide compound of this application and methods of preparing the same are also provided. In particular, in some aspects, a benzoate salt of a compound of 5-[3-(3-hydroxyphenoxy)azetidin-1-yl]-5-methyl-2,2-diphenyl-hexanenitrile having the formula I

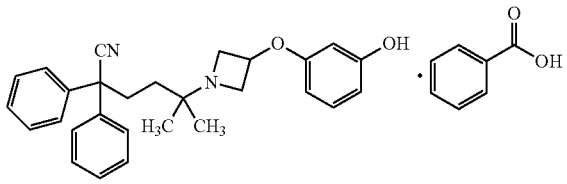 [SMILES: CC(C)(CCC(C#N)(c1ccccc1)c1ccccc1)N1CC(Oc2cccc(O)c2)C1 ; O=C(O)c1ccccc1]

is provided. The compound of formula I can be prepared by, for example, reacting a benzyl coupled compound of formula III

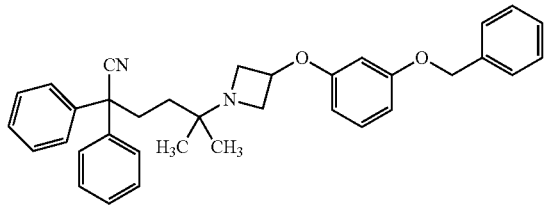 [SMILES: CC(C)(CCC(C#N)(c1ccccc1)c1ccccc1)N1CC(Oc2cccc(OCc3ccccc3)c2)C1]

with ethyl acetate and activated charcoal to form a mixture, filtering the mixture, adding acetic acid and subjecting the mixture to catalytic hydrogenation and adding toluene and benzoic acid to the mixture to form the compound of formula I.

In other aspects, a benzyl coupled compound of formula III

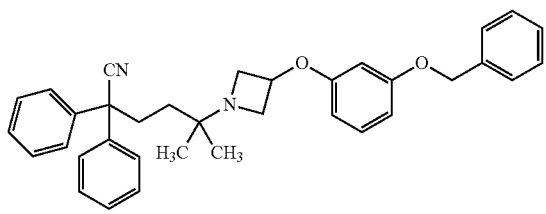 [SMILES: CC(C)(CCC(C#N)(c1ccccc1)c1ccccc1)N1CC(Oc2cccc(OCc3ccccc3)c2)C1]

is provided. The compound of formula III can be prepared, for example, by reacting an azetidine mesyl hydrochloride of formula IV

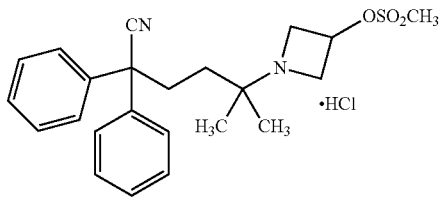

with a reagent comprising benzyl resorcinol (e.g., 3-(benzyloxy)phenol) of formula V

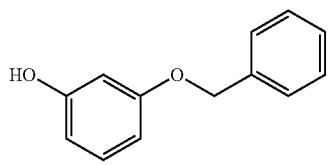 [SMILES: Oc1cccc(OCc2ccccc2)c1]

to form a benzyl coupled compound of formula III.

In some non-limiting embodiments, the methods for preparing a carboxamide compound include the steps of: (i) reacting 3-methyl-3-buten-1-ol with methanesulfonyl chloride and diphenylacetonitrile to form a diphenyl alkene; (ii) reacting the diphenyl alkene with chloroacetonitrile to form a diphenyl chloro amide; (iii) reacting the diphenyl chloro amide with thiourea to form a diphenyl amine; (iv) reacting the diphenyl amine with epichlorohydrin to form an azetidine alcohol; (v) reacting the azetidine alcohol with methanesulfonyl chloride to form azetidine mesyl HCl; (vi) reacting the azetidine mesyl HCl with benzyl resorcinol to form a benzyl coupled compound; (vii) mixing the benzyl coupled compound with ethyl acetate and filtering, adding acetic acid and subjecting the mixture to catalytic hydrogenation, adding toluene and benzoic acid to the mixture to form 5-[3-(3-hydroxyphenoxy)azetidin-1-yl]-5-methyl-2,2-diphenylhexanenitrile benzoate; and (viii) reacting 5-[3-(3-hydroxyphenoxy)azetidin-1-yl]-5-methyl-2,2-diphenyl-hexanenitrile benzoate with a reagent and hydrochloric acid to form 5-[3-(3-hydroxyphenoxy)azetidin-1-yl]-5-methyl-2,2-diphenylhexanamide hydrochloride.

Various aspects of the present disclosure may be further characterized by one or more of the following clauses:

Clause 1: A method for preparing a carboxamide compound, the method comprising reacting 5-[3-(3-hydroxyphenoxy)azetidin-1-yl]-5-methyl-2,2-diphenylhexanenitrile benzoate with a reagent and hydrochloric acid to form the carboxamide compound comprising 5-[3-(3-hydroxyphenoxy)azetidin-1-yl]-5-methyl-2,2-diphenylhexanamide hydrochloride.

Clause 2: The method for preparing the carboxamide compound according to clause 1, wherein the reagent comprises a base and an alcohol.

Clause 3: The method for preparing the carboxamide compound according to clause 2, wherein the base comprises potassium hydroxide and the alcohol comprises a tertiary amyl alcohol.

Clause 4: The method for preparing the carboxamide compound according to any one of clauses 1-3, further comprising washing the 5-[3-(3-hydroxyphenoxy)azetidin-1-yl]-5-methyl-2,2-diphenylhexanamide hydrochloride with a mixture comprising an alcohol and an ether.

Clause 5: The method for preparing the carboxamide compound according to clause 4, wherein the alcohol in the mixture comprises tertiary amyl alcohol and the ether in the mixture comprises methyl tert-butyl ether.

Clause 6: The method for preparing the carboxamide compound according to any one of clauses 1-5, wherein the 5-[3-(3-hydroxyphenoxy)azetidin-1-yl]-5-methyl-2,2-diphenylhexanenitrile benzoate is prepared by reacting a benzyl coupled compound comprising 5-(3-(3-(benzyloxy)phenoxy)azetidin-1-yl)-5-methyl-2,2-diphenylhexanenitrile with ethyl acetate and/or acetic acid and activated charcoal to form a mixture, filtering and subjecting the resulting mixture to catalytic hydrogenation, washing with sodium hydroxide and adding toluene and benzoic acid to the mixture to form the 5-[3-(3-hydroxyphenoxy)azetidin-1-yl]-5-methyl-2,2-diphenylhexanenitrile benzoate.

Clause 7: The method for preparing the carboxamide compound according to clause 6, wherein the benzyl coupled compound is prepared by reacting an azetidine mesyl HCl comprising 1-(5-cyano-2-methyl-5,5-diphenyl-pentan-2-yl)azetidin-3-yl methanesulfonate hydrochloride with a reagent comprising benzyl resorcinol.

Clause 8: The method for preparing the carboxamide compound according to clause 7, wherein: (i) the reagent further comprises acetonitrile and cesium carbonate or potassium carbonate; (ii) the benzyl resorcinol is prepared by reacting resorcinol with benzyl chloride to form benzyl resorcinol; or (iii) the benzyl resorcinol is prepared by reacting resorcinol with benzyl chloride, potassium carbonate and dimethylformamide.

Clause 9: The method for preparing the carboxamide compound according to clause 7 or clause 8, wherein: (i) the azetidine mesyl HCl is prepared by reacting azetidine alcohol with methanesulfonyl chloride; or (ii) the azetidine mesyl HCl is prepared by reacting azetidine alcohol with methanesulfonyl chloride, triethylamine, HCl in isopropyl alcohol and toluene.

Clause 10: The method for preparing the carboxamide compound according to clause 9, wherein: (i) the azetidine alcohol is prepared by reacting a diphenyl amine with epichlorohydrin; or (ii) the azetidine alcohol is prepared by reacting a diphenyl amine with epichlorohydrin, isopropyl alcohol, acetic acid, toluene and heptane.

Clause 11: The method for preparing the carboxamide compound according to clause 10, wherein: (i) the diphenyl amine is prepared by reacting diphenyl chloro amide with thiourea; or (ii) the diphenyl amine is prepared by reacting diphenyl chloro amide with thiourea, acetic acid and isopropyl alcohol.

Clause 12: The method for preparing the carboxamide compound according to clause 11, wherein: (i) the diphenyl chloro amide is prepared by reacting a diphenyl alkene with chloroacetonitrile; or (ii) the diphenyl chloro amide is prepared by reacting a diphenyl alkene with chloroacetonitrile, acetic acid and sulfuric acid.

Clause 13: The method for preparing the carboxamide compound according to clause 12, wherein: (i) the diphenyl alkene is prepared by reacting 3-methyl-3-buten-1-ol with methanesulfonyl chloride and diphenylacetonitrile; (ii) the diphenyl alkene is prepared by reacting 3-methyl-3-buten-1-ol with methanesulfonyl chloride to form a mesyl alkene intermediate, and treating the mesyl alkene intermediate with diphenylacetonitrile, tetrabutyl ammonium bromide and sodium hydroxide; or (iii) the diphenyl alkene is prepared by reacting 3-methyl-3-buten-1-ol with methanesulfonyl chloride to form a mesyl alkene intermediate, and treating the mesyl alkene intermediate with diphenylacetonitrile, tetrabutyl ammonium bromide and sodium hydroxide, toluene and triethylamine.

Clause 14: A method for preparing a carboxamide compound, the method comprising the steps of: (i) reacting 3-methyl-3-buten-1-ol with methanesulfonyl chloride and diphenylacetonitrile to form a diphenyl alkene; (ii) reacting the diphenyl alkene with chloroacetonitrile to form a diphenyl chloro amide; (iii) reacting the diphenyl chloro amide with thiourea to form a diphenyl amine; (iv) reacting the diphenyl amine with epichlorohydrin to form azetidine alcohol; (v) reacting the azeditine alcohol with methanesulfonyl chloride to form azetidine mesyl HCl; (vi) reacting the azetidine mesyl HCl with benzyl resorcinol to form a benzyl coupled compound; (vii) reacting the benzyl coupled compound with ethyl acetate and/or acetic acid and filtering to form a mixture; (viii) subjecting the mixture to catalytic hydrogenation; (ix) adding sodium hydroxide, toluene and benzoic acid to the mixture in step (viii) to form 5-[3-(3-hydroxyphenoxy)azetidin-1-yl]-5-methyl-2,2-diphenyl-hexanenitrile benzoate; and (x) reacting 5-[3-(3-hydroxy-phenoxy)azetidin-1-yl]-5-methyl-2,2-diphenylhexanenitrile benzoate with a reagent and hydrochloric acid to form 5-[3-(3-hydroxyphenoxy)azetidin-1-yl]-5-methyl-2,2-diphenylhexanamide hydrochloride.

Clause 15: A method of preparing a carboxamide compound, the method comprising reacting 5-[3-(3-hydroxyphenoxy)azetidin-1-yl]-5-methyl-2,2-diphenylhexanenitrile benzoate of formula I

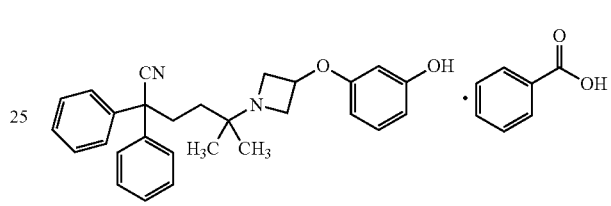

with a reagent and hydrochloric acid to form the carboxamide compound comprising 5-[3-(3-hydroxyphenoxy)azetidin-1-yl]-5-methyl-2,2-diphenylhexanamide hydrochloride of formula II

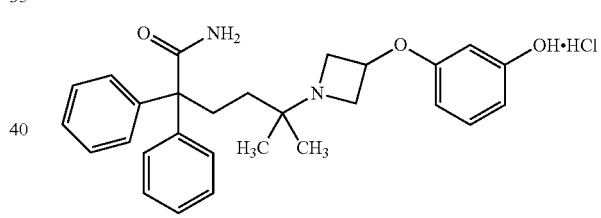

Clause 16: The method of preparing the carboxamide compound according to clause 15, wherein the 5-[3-(3-hydroxyphenoxy)azetidin-1-yl]-5-methyl-2,2-diphenyl-hexanenitrile benzoate of formula I is prepared by reacting a benzyl coupled compound of formula III

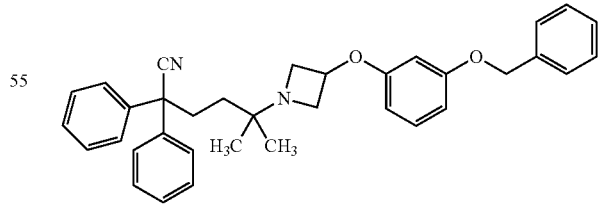

with ethyl acetate and/or acetic acid to form a mixture, subjecting the mixture to catalytic hydrogenation, washing with sodium hydroxide and adding toluene and benzoic acid to the mixture to form the 5-[3-(3-hydroxyphenoxy)azetidin-1-yl]-5-methyl-2,2-diphenylhexanenitrile benzoate of formula I

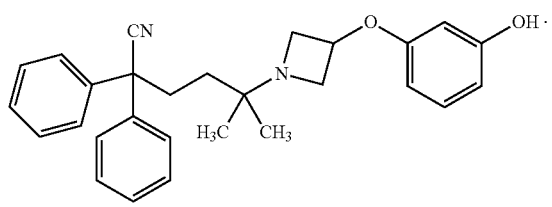

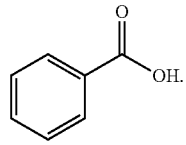

Clause 17: The method of preparing the carboxamide compound according to clause 16, wherein the benzyl coupled compound of formula IH

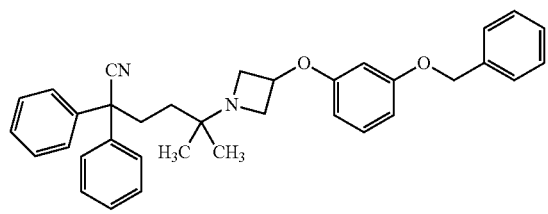 [SMILES: CC(C)(CCC(C#N)(c1ccccc1)c1ccccc1)N1CC(Oc2cccc(OCc3ccccc3)c2)C1]

is prepared by reacting an azetidine mesyl HCl of formula IV

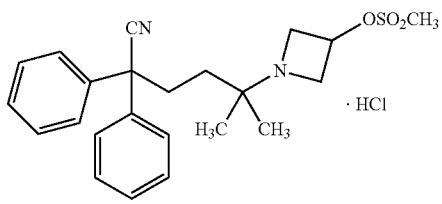

with a reagent comprising benzyl resorcinol of formula V

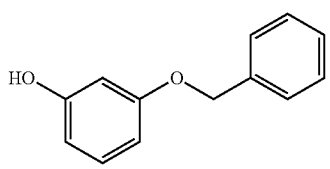

Clause 18: The method of preparing the carboxamide compound according to clause 17, wherein: (i) the reagent further comprises acetonitrile and cesium carbonate or potassium carbonate; (ii) the benzyl resorcinol is prepared by reacting resorcinol with benzyl chloride; or (iii) the benzyl resorcinol is prepared by reacting resorcinol with benzyl chloride, potassium carbonate and dimethylformamide.

Clause 19: The method of preparing the carboxamide compound according to clause 17 or clause 18, wherein: (i) the azetidine mesyl HCl of formula IV

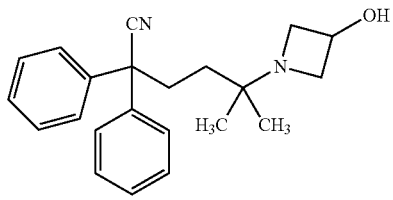 [SMILES: CC(C)(CCC(C#N)(c1ccccc1)c1ccccc1)N1CC(O)C1]

is prepared by reacting azetidine alcohol of formula VI

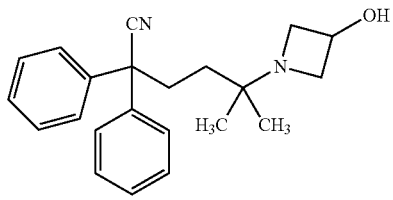 [SMILES: CC(C)(CCC(C#N)(c1ccccc1)c1ccccc1)N1CC(O)C1]

with methanesulfonyl chloride to obtain the azetidine mesyl HCl of formula IV; or (ii) the azetidine mesyl HCl is prepared by reacting azetidine alcohol of formula VI with methanesulfonyl chloride triethylamine, HCl in isopropyl alcohol and toluene to obtain the azetidine mesyl HCl of formula IV.

Clause 20: The method of preparing the carboxamide compound according to clause 19, wherein: (i) the azetidine alcohol of formula VI

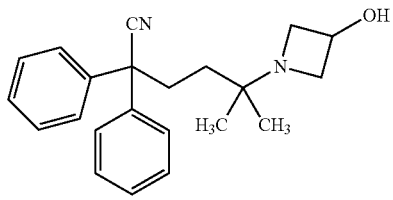 [SMILES: CC(C)(CCC(C#N)(c1ccccc1)c1ccccc1)N1CC(O)C1]

is prepared by reacting a diphenyl amine of formula VII

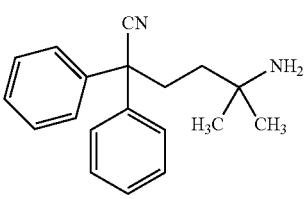 [SMILES: CC(C)(N)CCC(C#N)(c1ccccc1)c1ccccc1]

with epichlorohydrin to form the azetidine alcohol of formula VI; or (ii) the azetidine alcohol of formula VI is prepared by reacting a diphenyl amine of formula VII with epichlorohydrin, isopropyl alcohol, acetic acid, toluene and heptane to form the azetidine alcohol.

Clause 21: The method of preparing the carboxamide compound according to clause 20, wherein the diphenyl amine of formula VII

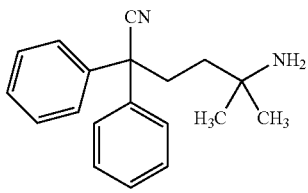 [SMILES: CC(C)(N)CCC(C#N)(c1ccccc1)c1ccccc1]

is prepared by reacting diphenyl chloro amide of formula VIII

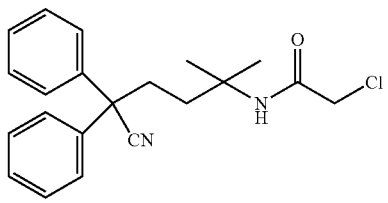 [SMILES: CC(C)(CCC(C#N)(c1ccccc1)c1ccccc1)NC(=O)CCl]

with thiourea; or (ii) the diphenyl amine is prepared by reacting diphenyl chloro amide of formula VIII with thiourea, acetic acid and isopropyl alcohol.

Clause 22: The method of preparing the carboxamide compound according to clause 21, wherein: (i) the diphenyl chloro amide of formula VIII

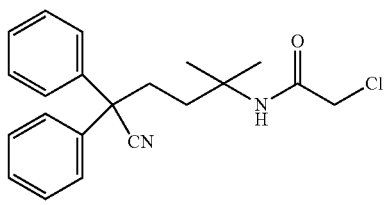 [SMILES: CC(C)(CCC(C#N)(c1ccccc1)c1ccccc1)NC(=O)CCl]

is prepared by reacting a diphenyl alkene of formula IX

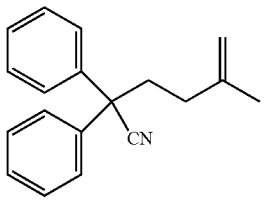 [SMILES: C=C(C)CCC(C#N)(c1ccccc1)c1ccccc1]

with chloroacetonitrile to form the diphenyl chloro amide of formula VIII; or (ii) the diphenyl chloro amide of formula VIII is prepared by reacting a diphenyl alkene of formula IX with chloroacetonitrile acetic acid and sulfuric acid.

Clause 23: The method of preparing the carboxamide compound according to clause 22, wherein: (i) the diphenyl alkene of formula IX

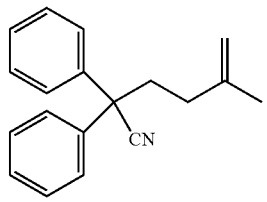 [SMILES: C=C(C)CCC(C#N)(c1ccccc1)c1ccccc1]

is prepared by reacting 3-methyl-3-buten-1-ol of formula X

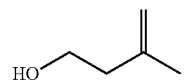

with methanesulfonyl chloride and diphenylacetonitrile; (ii) the diphenyl alkene of formula IX is prepared by reacting 3-methyl-3-buten-1-ol of formula X with methanesulfonyl chloride to form a mesyl alkene intermediate, treating the mesyl alkene intermediate with diphenylacetonitrile, tetrabutyl ammonium bromide and sodium hydroxide; or (iii) the diphenyl alkene of formula IX is prepared by reacting 3-methyl-3-buten-1-ol with methanesulfonyl chloride to form a mesyl alkene, treating the mesyl alkene intermediate with diphenylacetonitrile, tetrabutyl ammonium bromide and sodium hydroxide, toluene and triethylamine.

Clause 24: A benzoate salt of a compound of 5-[3-(3-hydroxyphenoxy)azetidin-1-yl]-5-methyl-2,2-diphenyl-hexanenitrile having the formula I

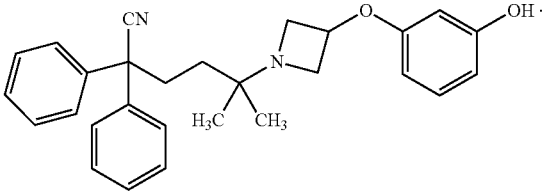

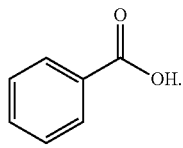

Clause 25: A benzyl coupled compound of formula III

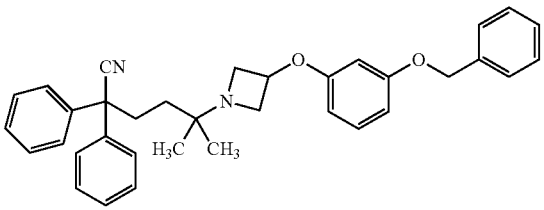

Clause 26: A method for preparing a benzyl coupled compound of formula III

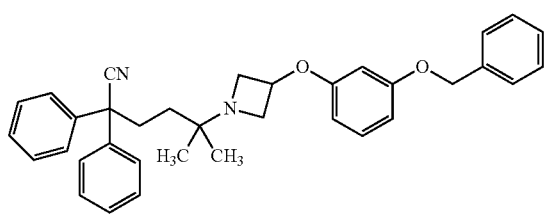

the method comprising, reacting an azetidine mesyl hydrochloride of formula IV

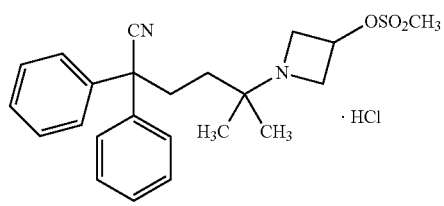

with a reagent comprising benzyl resorcinol of formula V

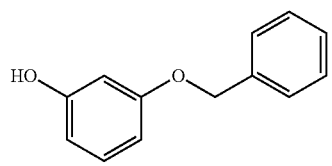 [SMILES: Oc1cccc(OCc2ccccc2)c1]

to form the benzyl coupled compound of formula III.

Clause 27: The method according to clause 26, wherein: (i) the reagent further comprises acetonitrile, potassium carbonate or cesium carbonate; (ii) the benzyl resorcinol is prepared by reacting resorcinol with benzyl chloride to form benzyl resorcinol; or (iii) the benzyl resorcinol is prepared by reacting resorcinol with benzyl chloride, potassium carbonate and dimethylformamide.

Clause 28: A method for preparing a coupled compound benzoate of formula I

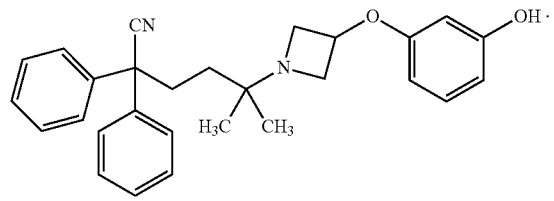

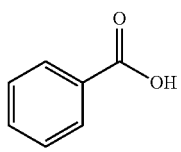

the method comprising reacting a benzyl coupled compound of formula III

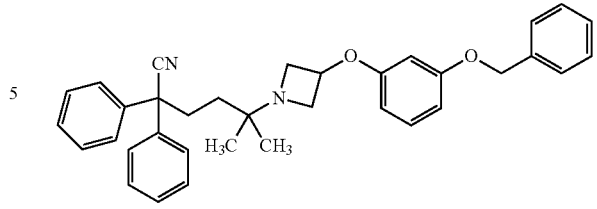

with ethyl acetate and/or acetic acid and activated charcoal and filtering to form a mixture, subjecting the mixture to catalytic hydrogenation and adding sodium hydroxide, toluene and benzoic acid to the mixture to form the compound of formula I

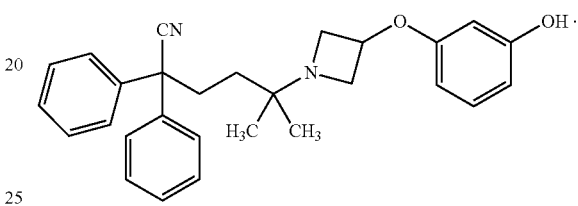

Clause 29: The method for preparing the carboxamide compound according to any one of clauses 1-13, wherein the carboxamide compound comprising 5-[3-(3-hydroxyphenoxy)azetidin-1-yl]-5-methyl-2,2-diphenylhexanamide hydrochloride is micronized.

Clause 30: The method for preparing the carboxamide compound according to any one of clauses 1-13 or clause 29, wherein the carboxamide compound has a particle size distribution D90 in the range of from about 75 micrometers to about 350 micrometers.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWING

In part, other aspects, features, benefits and advantages of the embodiments will be apparent with regard to the following description, appended claims and accompanying drawings where:

DETAILED DESCRIPTION

Figure 1A:
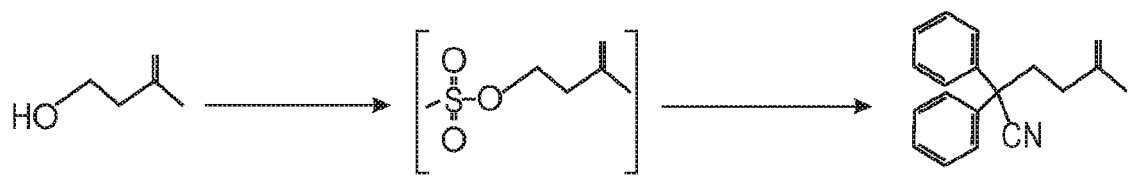
FIGS. 1A, 1B, 1C, and 1D illustrate a stepwise reaction for synthesizing azetidine alcohol, the steps including the preparation of diphenyl alkene, diphenyl chloro amide and diphenyl amine to form azetidine alcohol as shown in one embodiment of this disclosure.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

In this application, the section headings below should not be restricted and can be interchanged with other section headings.

Definitions

It is noted that, as used in this specification and the appended claims, the singular forms "a", "an", and "the" include plural referents unless expressly and unequivocally limited to one referent. Thus, for example, reference to "an alkanolamine" includes one, two, three or more alkanolamines.

The terms "having", "containing", "including", "comprising" and the like are used herein to refer to open ended terms that indicate the presence of stated elements or features, but do not preclude additional elements or features.

The term "excipient" is used herein to describe any ingredient other than the hydrochloride salt of this application. The choice of excipient will to a large extent depend on the particular mode of administration.

A "pharmaceutically acceptable carrier" is meant as a material that is not biologically or otherwise undesirable, e.g., the material may be administered to a subject without causing any undesirable biological effects or interacting in a deleterious manner with any of the other components of the pharmaceutical composition in which it is contained.

The term "solvate" is used herein to describe a molecular complex comprising the hydrochloride salt of this disclosure and a stoichiometric amount of one or more pharmaceutically acceptable solvent molecules, for example, ethanol. Examples of solvents that form solvates include, but are not limited to, water, isopropanol, ethanol, methanol, DMSO, ethyl acetate, acetic acid, and ethanolamine.

The solvent may be inorganic solvents such as, for example, water in which case the solvate may be a hydrate. Alternatively, the solvent may be an organic solvent, such as ethanol. The compound of the disclosure may be a true solvate, while in other cases, the compound of the disclosure may merely retain adventitious water and/or organic solvent or be a mixture of water plus some adventitious organic solvent.

The term "treatment" includes references to curative, palliative and prophylactic treatment.

The term "reagent" includes compound added to a chemical system to cause a chemical reaction. In some embodiments, a reagent can include a reactant.

Methods and Intermediates for Making a Carboxamide Compound

Methods for preparing 5-[3-(3-hydroxyphenoxy)azetidin-1-yl]-5-methyl-2,2-diphenyl-hexanamide hydrochloride are described in this application. In particular, 5-[3-(3-hydroxyphenoxy)azetidin-1-yl]-5-methyl-2,2-diphenyl-hexanamide hydrochloride, a carboxamide hydrochloride of formula II

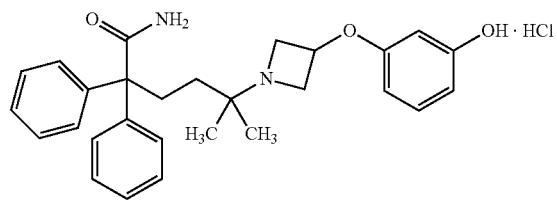

can be prepared by reacting 5-[3-(3-hydroxyphenoxy)azetidin-1-yl]-5-methyl-2,2-diphenyl-hexanenitrile benzoate of formula I (a benzoate compound of formula I)

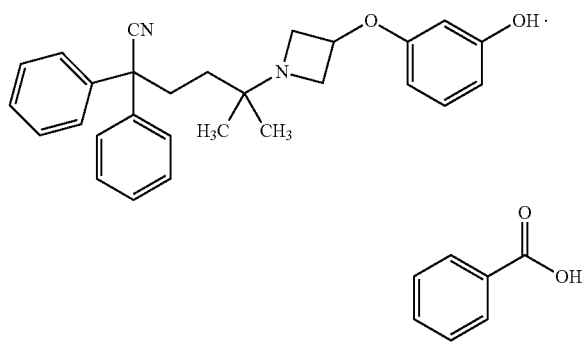

with a reagent and hydrochloric acid to form the carboxamide compound described in this application as illustrated in the Reaction Scheme 1 below:

Reaction Scheme 1 -Preparation of Crude Carboxamide Hydrochloride

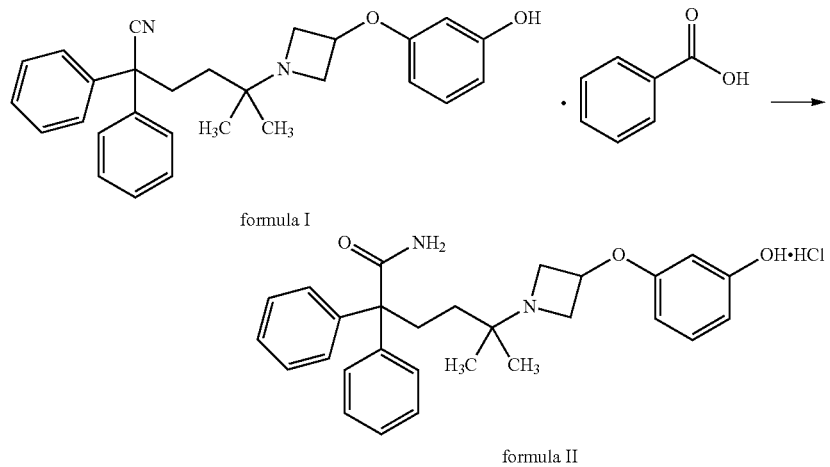

formula I formula II

The coupled benzoate compound of formula I can be reacted with KOH, 2-methyl-2-butanol, water, then HCl aqueous, HCl, and TBME to obtain the crude carboxamide hydrochloride of formula II. The benzoate salt of the nitrile provides for easier purification of the nitrile.

The reagents useful in the preparation of 5-[3-(3-hydroxyphenoxy)azetidin-1-yl]-5-methyl-2,2-diphenyl-hexanamide hydrochloride include a base and an alcohol. In some embodiments, a useful base includes potassium hydroxide, while a useful alcohol includes tertiary amyl alcohol also known as 2-methyl-2-butanol. The reaction of the benzoate compound of formula II in tertiary amyl alcohol and potassium hydroxide can be carried in a temperature range from about 85±5° C. to about 103±2° C. In a later stage, the temperature of 103±2° C. can be maintained in that range for from about 30 hours to about 65 hours. A cooling period to about room temperature is followed by adjusting the pH to a range from about 6.5 to about 8.0. Hydrochloric acid is added to the product of this initial reaction to form a crude carboxamide hydrochloride compound of formula II. The initially isolated crude carboxamide hydrochloride compound of formula II can be washed with an alcohol and then washed with, or slurried in an ether. In some embodiments, the alcohol can be tertiary amyl alcohol and the ether can be methyl tertiary butyl ether.

In various embodiments, the crude 5-[3-(3-hydroxyphenoxy)azetidin-1-yl]-5-methyl-2,2-diphenylhexanamide hydrochloride can be further purified by treating this carboxamide hydrochloride compound with a slurry of activated charcoal, for example, commercially available ENOPC, PF133 or PF511 SPL (A) carbon, in isopropyl alcohol and water at 85±5° C. and filtering as illustrated in the Reaction Scheme 2 below:

Reaction Scheme 2 - Puridication of Carboxamide Hydrochloride

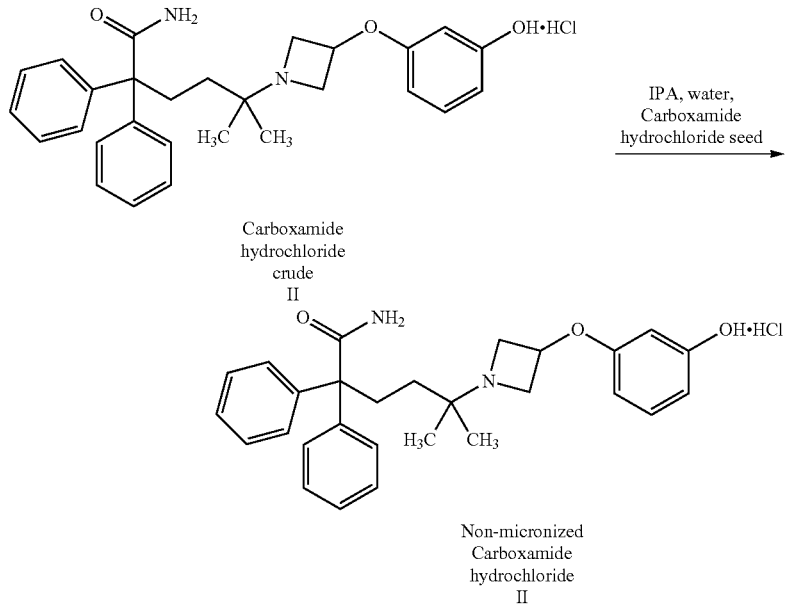

Carboxamide
hydrochloride
crude
II

IPA, water,
Carboxamide
hydrochloride seed

Non-micronized
Carboxamide
hydrochloride
II

Adding seeds of pure crystalline 5-[3-(3-hydroxyphenoxy) azetidin-1-yl]-5-methyl-2,2-diphenyl-hexanamide hydrochloride results in a carboxamide hydrochloride product of high purity In some embodiments, the results produced a product having a particle size distribution D90 in the range from about 75 micrometers to about 350 micrometers. In a further embodiment, controlling the cooling profile results in a product with acceptable solvent levels.

In some aspects, the 5-[3-(3-hydroxyphenoxy)azetidin-1-yl]-5-methyl-2,2-diphenyl-hexanenitrile benzoate of formula I can be prepared by reacting a benzyl coupled compound 5-(3-(3-(benzyloxy)phenoxy)azetidin-1-yl)-5-methyl-2,2-diphenylhexanenitrile of formula III

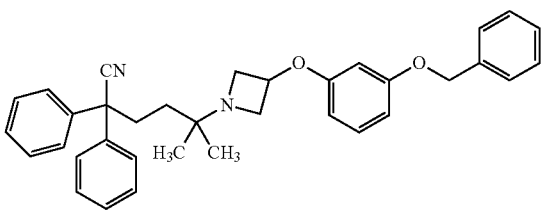 [SMILES: CC(C)(CCC(C#N)(c1ccccc1)c1ccccc1)N1CC(Oc2cccc(OCc3ccccc3)c2)C1]

with ethyl acetate and activated charcoal to form a mixture, filtering, adding acetic acid and subjecting the mixture to catalytic hydrogenation and adding toluene and benzoic acid to the mixture to form the 5-[3-(3-hydroxyphenoxy)azetidin-1-yl]-5-methyl-2,2-diphenylhexanenitrile benzoate of formula I as illustrated in the Reaction Scheme 3 below:

Reaction Scheme 3 - Preparation of the Coupled Compound Benzoate

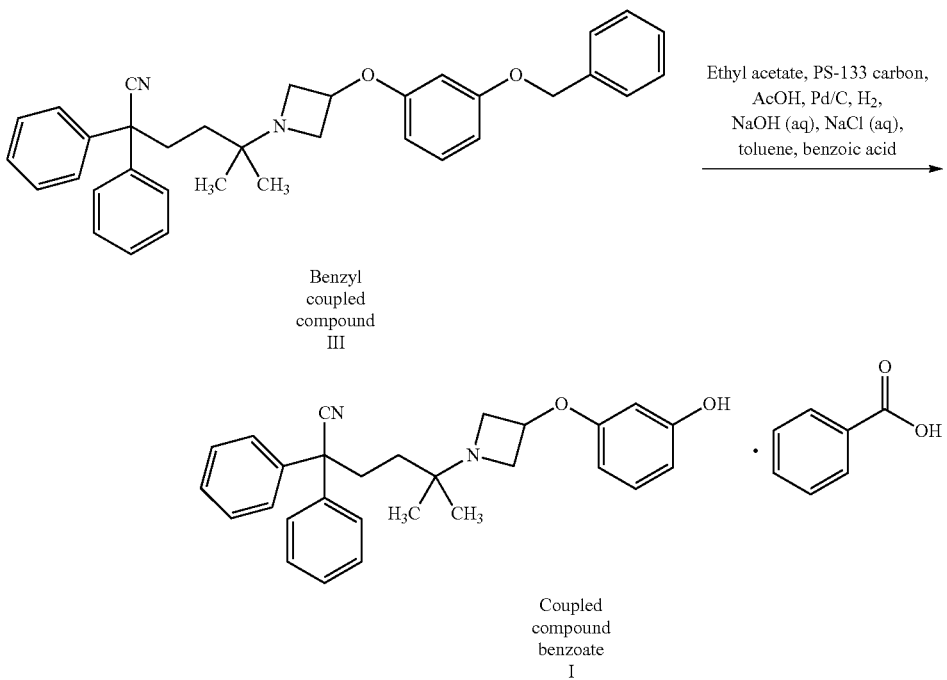

In some embodiments, the benzyl coupled compound of formula III is prepared by reacting an azetidine mesyl HCl 1-(5-cyano-2-methyl-5,5-diphenylpentan-2-yl)azetidin-3-yl methanesulfonate hydrochloride with a reagent comprising benzyl resorcinol as illustrated in the Reaction Scheme 4 below:

Reaction Scheme 4 - Preparation of the Benzyl Coupled Compound

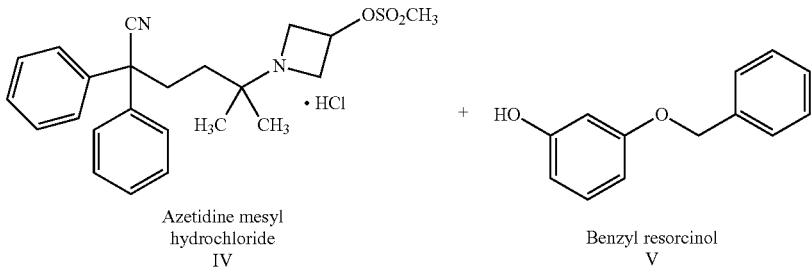

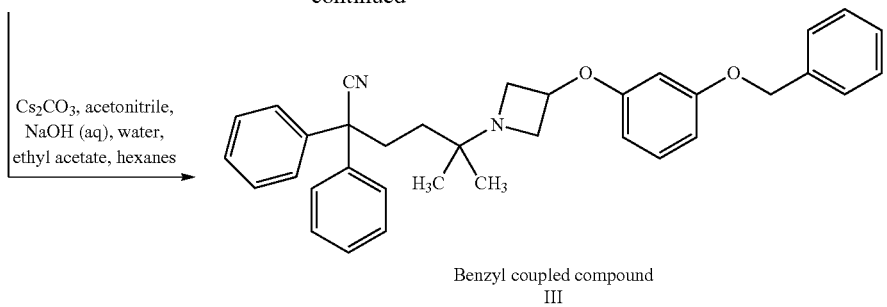

Benzyl coupled compound
III

In Reaction Scheme 4, the azetidine mesyl hydrochloride of formula IV

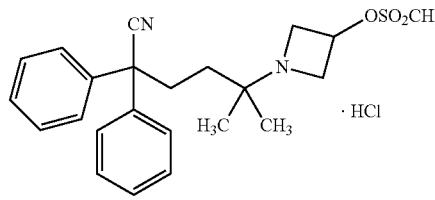

is reacted with benzyl resorcinol of formula V

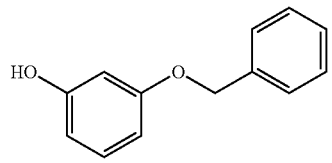 [SMILES: Oc1cccc(OCc2ccccc2)c1]

The reagent can comprise benzyl resorcinol and, in some aspects, acetonitrile, a carbonate salt of either cesium or potassium, sodium hydroxide, water, ethyl acetate, hexanes or a mixture thereof. The order of addition of reagents in this step overcomes the need for specific equipment (e.g., a bespoke/unusual agitator) and allows the step to be run in a general purpose reactor.

Benzyl resorcinol is commercially available and can be obtained commercially, for example, from Sigma Aldrich Corp. In various embodiments, benzyl resorcinol of formula V can be prepared by reacting resorcinol with benzyl chloride to form benzyl resorcinol according to the Reaction Scheme 5 below:

Reaction Scheme 5 - Preparation of Benzyl Resorcinol

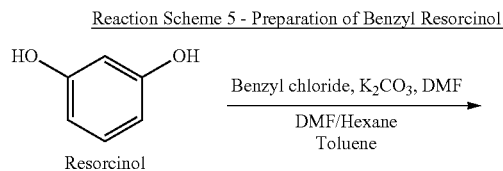

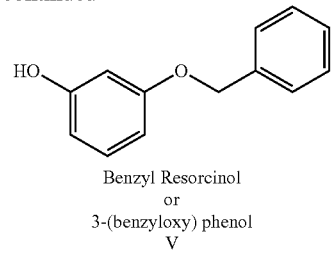

Benzyl Resorcinol
or
3-(benzyloxy) phenol
V

In certain aspects, the benzyl resorcinol is prepared by reacting resorcinol with benzyl chloride in a reagent which can include potassium carbonate, dimethylformamide, water, sodium hydroxide, toluene, hydrochloric acid, hexanes or a combination thereof. In some instances, benzyl resorcinol seeding material may also be added. For the conversion of the resorcinol to the benzyl resorcinol (V), the developed chemistry allows effective removal of remaining resorcinol starting material and dibenzyl impurity to give the benzyl resorcinol product in good yield and quality.

The azetidine mesyl hydrochloride of formula IV

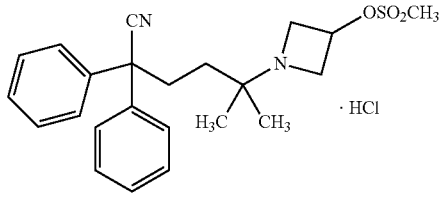

in some embodiments, can be prepared by reacting azetidine alcohol of formula VI

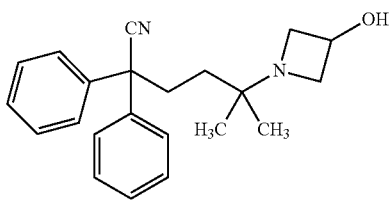 [SMILES: CC(C)(CCC(C#N)(c1ccccc1)c1ccccc1)N1CC(O)C1]

with methanesulfonyl chloride as illustrated in Reaction Scheme 6 below:

Reaction Scheme 6 - Preparation of Azetidine Mesyl Hydrochloride

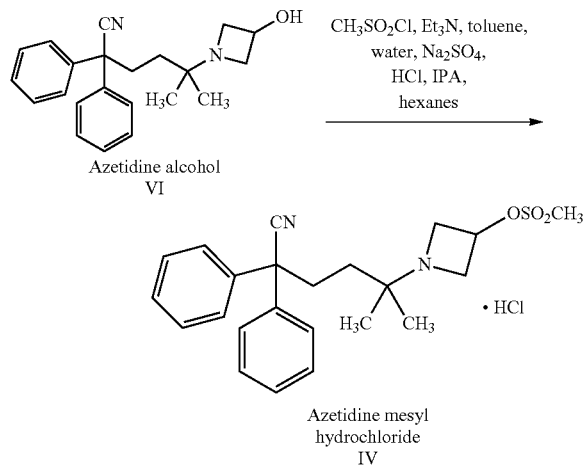

Reaction Scheme 7 - Preparation of Azetidine Alcohol

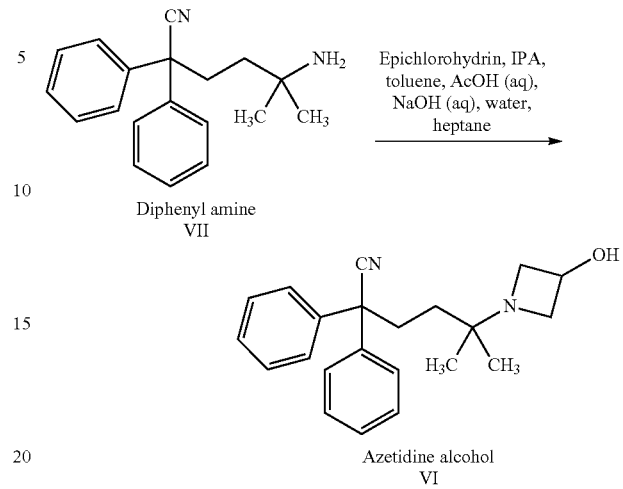

In other aspects, the azetidine mesyl HCl of formula IV can be prepared by reacting azetidine alcohol of formula VI with methanesulfonyl chloride in a reagent which includes triethylamine, hydrogen chloride in alcohol, sodium sulfate, hexanes, toluene, water or a mixture thereof. The hydrogen chloride, in some embodiments, can be anhydrous, for example, hydrogen chloride gas in isopropyl alcohol. The isolation of the azetidine mesyl as a hydrochloride salt provides material of good purity and reduces the level of impurities generated by the process up to this stage, including the potential impurities, if any are remaining, related to the genotoxic epichlorohydrin reactant used in the previous step.

In turn, in certain embodiments, azetidine alcohol of VI 5-(3-hydroxyazetidin-1-yl)-5-methyl-2,2-diphenylhexanenitrile

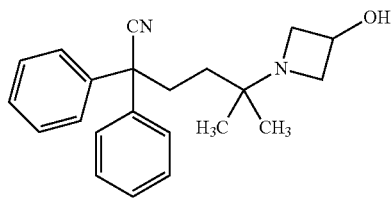 [SMILES: CC(C)(CCC(C#N)(c1ccccc1)c1ccccc1)N1CC(O)C1]

can be prepared by reacting a diphenyl amine of formula VII 5-amino-5-methyl-2,2-diphenylhexanenitrile

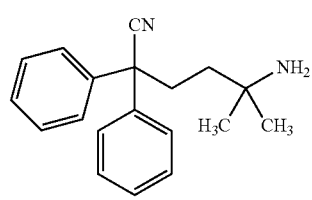 [SMILES: CC(C)(N)CCC(C#N)(c1ccccc1)c1ccccc1]

with epichlorohydrin as illustrated in the Reaction Scheme 7 below:

In other aspects, the azetidine alcohol of formula VI can be prepared by reacting a diphenyl amine of formula VII with epichlorohydrin, isopropyl alcohol, acetic acid (AcOH), sodium hydroxide, toluene, heptane, water or a mixture thereof. Acetic acid, sodium hydroxide and water are, in some instances, used for the extraction and pH adjustment of the reaction mass. Epichlorohydrin is commercially available and can be obtained, for example, from Sigma Aldrich Corp. In some embodiments, for the conversion of the diphenyl amine (VII) to the azetidine alcohol (VI), the use of an in-situ acetate salt (e.g., extraction of the amine into aqueous acetic acid) in the work-up can provide clean-up and separates the product from impurities related to the genotoxic epichlorohydrin reactant used in this reaction. The diphenyl amine of formula VII useful in preparing the azetidine alcohol of formula VI can be prepared, in some aspects, by reacting diphenyl chloro amide of formula VIII 2-chloro-N-(5-cyano-2-methyl-5,5-diphenylpentan-2-yl)acetamide

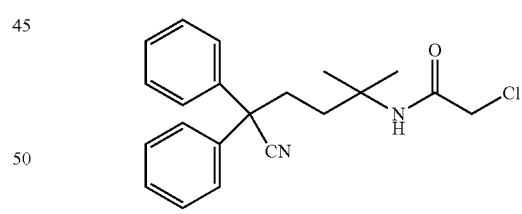

with thiourea as illustrated in the Reaction Scheme 8 below:

Scheme 8 - Preparation of Diphenyl Amine

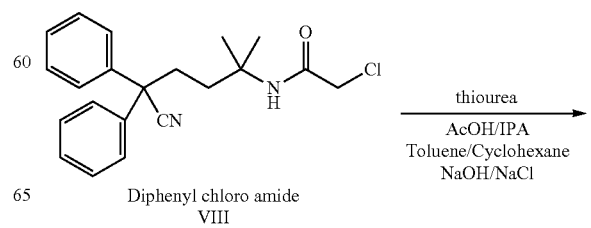

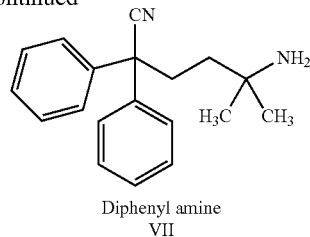

Diphenyl amine
VII

Thiourea is commercially available and can be obtained, for example, from Sigma Aldrich Corp.

In certain embodiments, the diphenyl amine is prepared by reacting diphenyl chloro amide with thiourea, acetic acid, isopropyl alcohol, sodium hydroxide, sodium chloride, cyclohexane, water or mixtures thereof. Acetic acid, sodium hydroxide and water are generally used in the removal of reaction by-products and pH adjustment. In some embodiments, for the conversion of the diphenyl chloro amide (VII) to the diphenyl amine (VII), the use of an in-situ acetate salt in the work-up provides for a clean-up and gives a product with a higher purity than what would have been otherwise obtained.

Diphenyl chloro amide of formula VIII, in some aspects, can be prepared by reacting a diphenyl alkene of formula IX

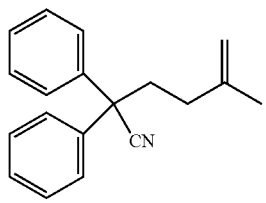 [SMILES: C=C(C)CCC(C#N)(c1ccccc1)c1ccccc1]

with chloroacetonitrile as illustrated in the Reaction Scheme 9 below:

Reaction Scheme 9 - Preparation of Diphenyl Chloro Amide

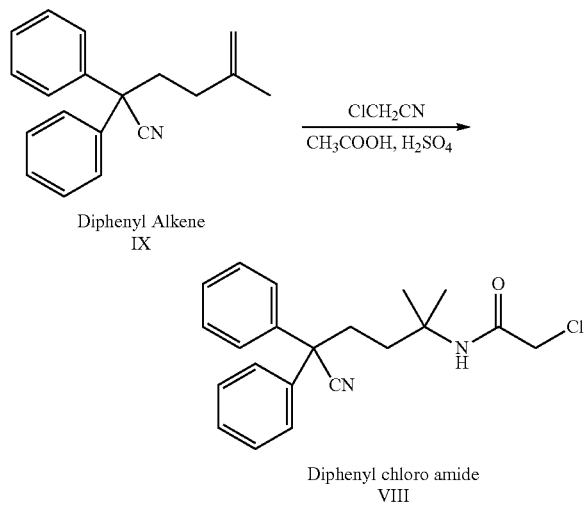

Diphenyl chloro amide
VIII

In certain aspects, the diphenyl chloro amide is prepared by reacting a diphenyl alkene of formula IX with chloroacetonitrile, acetic acid, sulfuric acid and water and mixtures thereof. By this stage in the synthesis, the gem-dimethyl functionality is in place. In some embodiments, for the conversion of the diphenyl alkene (IX) to the diphenyl chloro amide (VIII), isolation from water provides a good purity product.

Diphenyl alkene of formula IX, in some embodiments, can be prepared by reacting 3-methyl-3-buten-1-ol with methanesulfonyl chloride and diphenylacetonitrile. In other embodiments, the diphenyl alkene is prepared by reacting 3-methyl-3-buten-1-ol with methanesulfonyl chloride to form a mesyl alkene intermediate, and treating the mesyl alkene intermediate with diphenyl acetonitrile, tetrabutyl ammonium bromide (TBAB) and sodium hydroxide. In yet other aspects, the diphenyl alkene is prepared by reacting 3-methyl-3-buten-1-ol in toluene with methanesulfonyl chloride and triethylamine (TEA) to form a mesyl alkene intermediate, and treating the mesyl alkene intermediate with diphenyl acetonitrile, TBAB and sodium hydroxide, toluene, hydrochloric acid and water as illustrated in the Reaction Scheme 10 below:

Reaction Scheme 10 - Preparation of Diphenyl Alkene

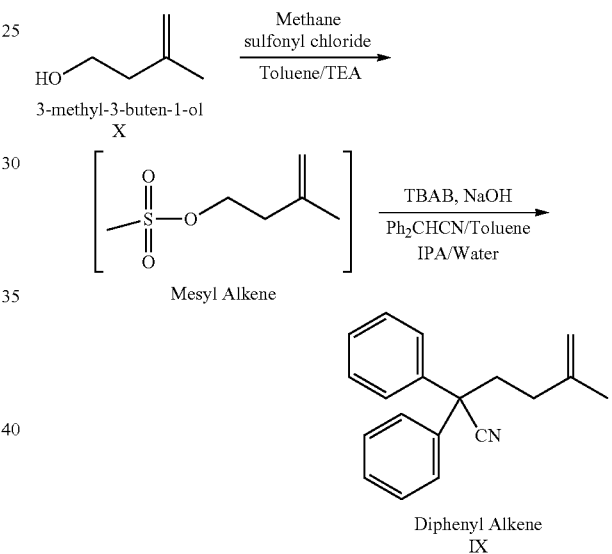

Diphenyl Alkene
IX

In some embodiments, the quantities of TEA, HCl and water may vary as they are used for the pH adjustment of the reaction mass. The use of toluene for both stages of the conversion of X to IX avoids the need for any solvent swaps (by distillation) at the mesyl alkene stage and results in the reaction being run safely on scale. For the isolation of the diphenyl alkene (IX), the use of isopropanol allows this material to be isolated in a straightforward manner that can be scaled up and provides material of usable purity.

Figure 1B:
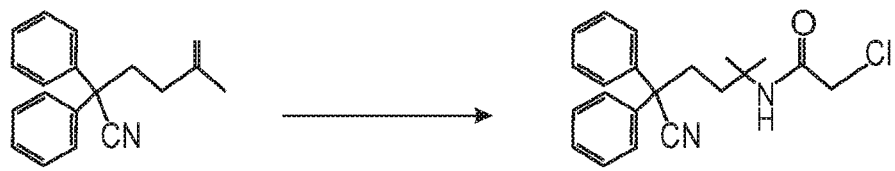
Figure 1C:
Figure 1D:
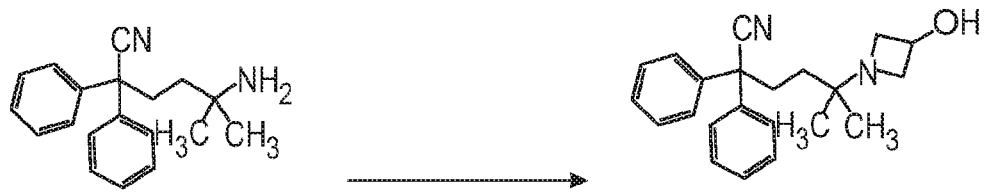
Figure 2A:
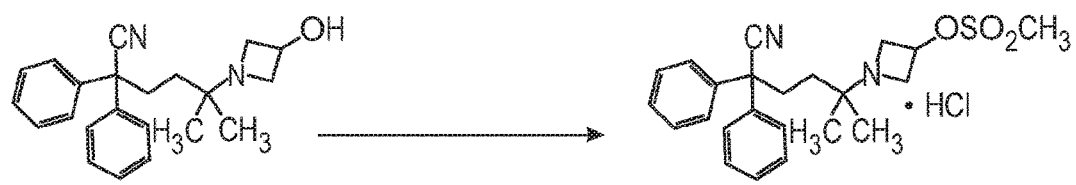
FIGS. 2A, 2B, and 2C illustrate a stepwise reaction for the preparation of a coupled benzoate compound, the steps including the preparation of azetidine mesyl hydrochloride, a benzyl coupled compound to form coupled compound benzoate.
Figure 2B:
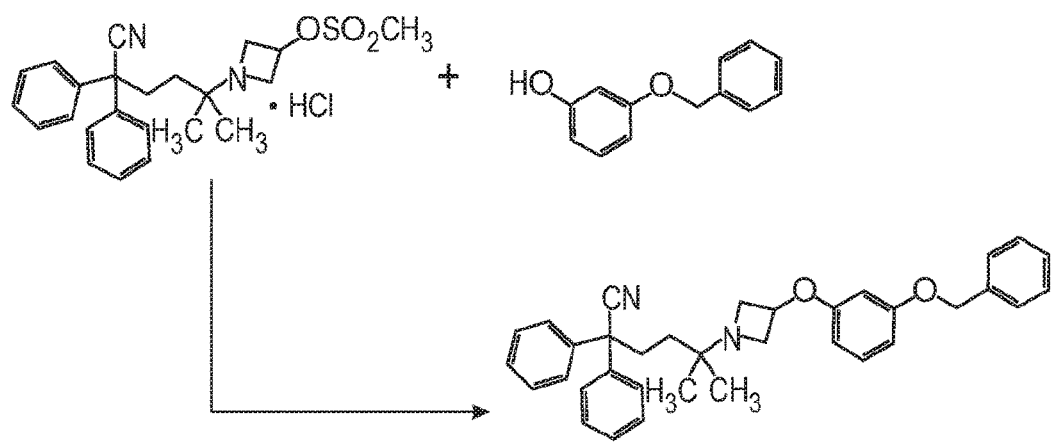
Figure 2C:
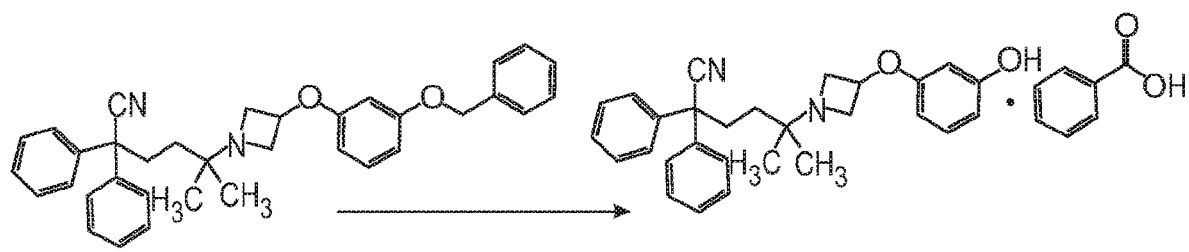
Figure 3:
FIG. 3 illustrates a reaction for the preparation of benzyl resorcinol.
Figure 4A:
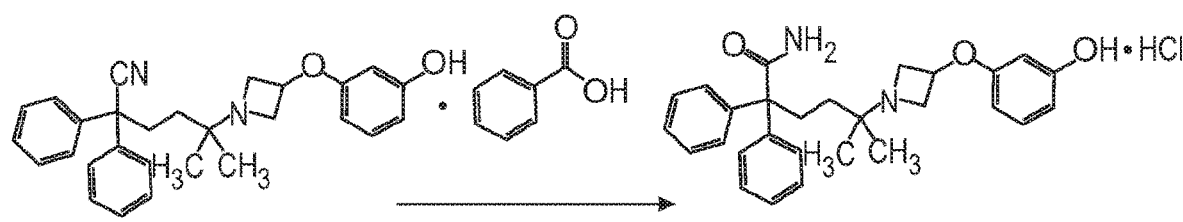
FIGS. 4A, 4B, and 4C illustrate a stepwise reaction for the preparation of micronized 5-[3-(3-hydroxy-phenoxy)azetidin-1-yl]-5-methyl-2,2-diphenylhexanamide hydrochloride, a carboxamide hydrochloride, the steps including the preparation of the crude carboxamide hydrochloride, the purification of the carboxamide hydrochloride and its micronization.
Figure 4B:
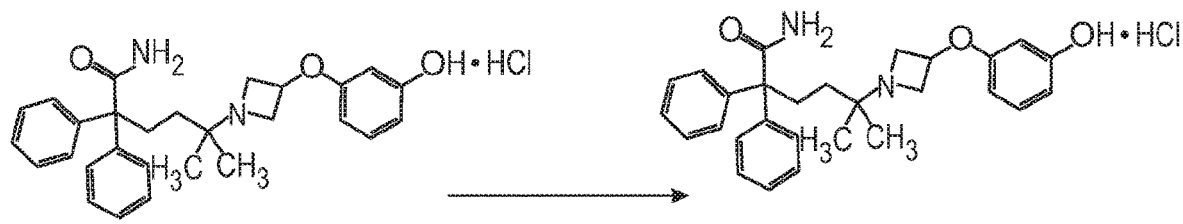
Figure 4C:
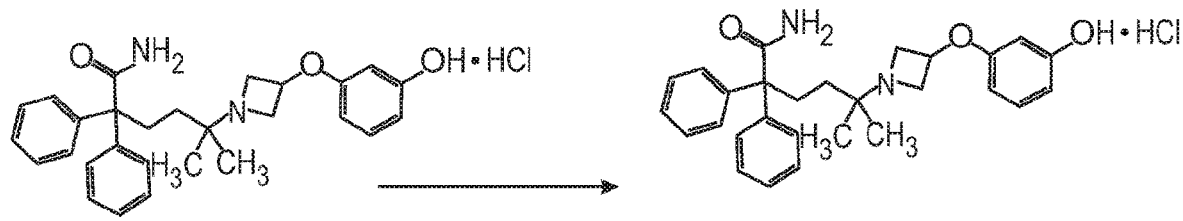

As illustrated in FIGS. 1A, 1B, 1C, 1D, 2A, 2B, 2C, 3, 4A, 4B, and 4C, this application provides a method for preparing a carboxamide compound, namely 5-[3-(3-hydroxyphenoxy)azetidin-1-yl]-5-methyl-2,2-diphenyl-hexanamide hydrochloride. The method illustrated in FIGS. 1A, 1B, 1C, 1D, 2A, 2B, 2C, 3, 4A, 4B, and 4C includes the steps of: (i) reacting 3-methyl-3-buten-1-ol with methanesulfonyl chloride and diphenylacetonitrile to form a diphenyl alkene; (ii) reacting the diphenyl alkene with chloroacetonitrile to form a diphenyl chloro amide; (iii) reacting the diphenyl chloro amide with thiourea to form a diphenyl amine; (iv) reacting the diphenyl amine with epichlorohydrin to form azetidine alcohol; (v) reacting the azeditine alcohol with methanesulfonyl chloride to form azetidine mesyl HCl; (vi) reacting the azetidine mesyl HCl with benzyl resorcinol to form a benzyl coupled compound; (vii) reacting the benzyl coupled compound with ethyl acetate and filtering, adding acetic acid and subjecting the mixture to catalytic hydrogenation, adding sodium hydroxide, toluene and benzoic acid to the mixture in a continuous process to form 5-[3-(3-hydroxyphenoxy)azetidin-1-yl]-5-methyl-2,2-diphenyl-hexanenitrile benzoate; and (x) reacting 5-[3-(3-hydroxyphenoxy)azetidin-1-yl]-5-methyl-2,2-diphenyl-hexanenitrile benzoate with a reagent and hydrochloric acid to form 5-[3-(3-hydroxyphenoxy)azetidin-1-yl]-5-methyl-2,2-diphenylhexanamide hydrochloride.

This application also provides a benzyl coupled compound of formula III

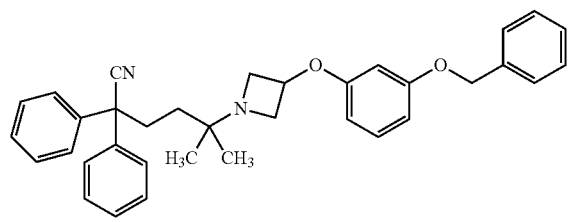 [SMILES: CC(C)(CCC(C#N)(c1ccccc1)c1ccccc1)N1CC(Oc2cccc(OCc3ccccc3)c2)C1]

The benzyl coupled compound of formula III is useful in the preparation of a benzoate salt of a compound of 5-[3-(3-hydroxyphenoxy)azetidin-1-yl]-5-methyl-2,2-diphenyl-hexanenitrile having the formula I

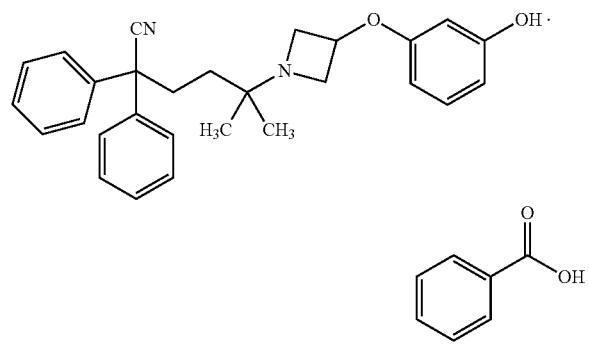

The benzyl coupled compound of formula III can be prepared by reacting an azetidine mesyl hydrochloride of formula IV

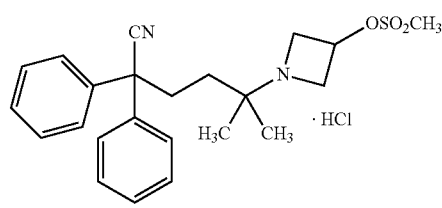

with a reagent comprising benzyl resorcinol of formula V

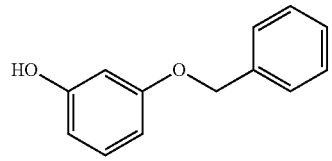 [SMILES: Oc1cccc(OCc2ccccc2)c1]

to form a benzyl coupled compound of formula III. In certain embodiments: (i) the reagent further comprises acetonitrile, potassium carbonate or cesium carbonate; (ii) the benzyl resorcinol is prepared by reacting resorcinol with benzyl chloride to form benzyl resorcinol; or (iii) the benzyl resorcinol is prepared by reacting resorcinol with benzyl chloride, potassium carbonate and dimethylformamide.

A benzoate salt of a compound of 5-[3-(3-hydroxyphenoxy)azetidin-1-yl]-5-methyl-2,2-diphenylhexanenitrile having the formula I

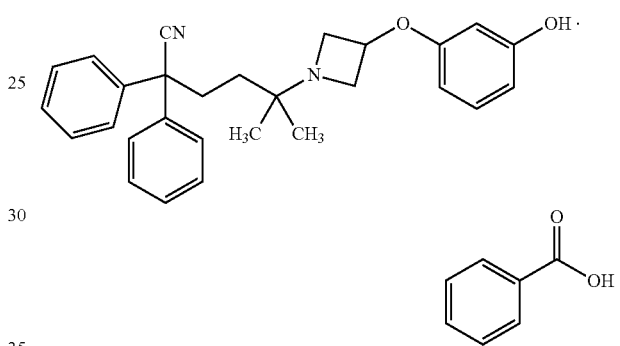

is also provided. The benzoate salt of formula I

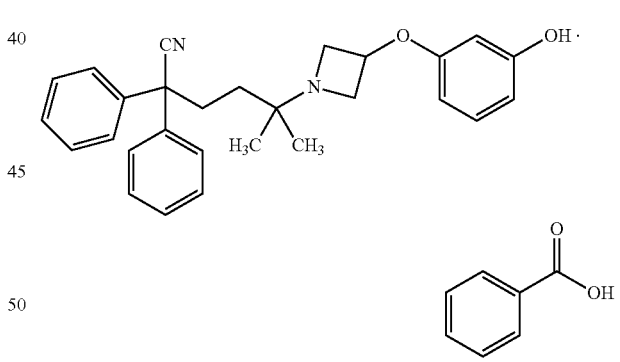

is prepared by reacting the benzyl coupled compound of formula III

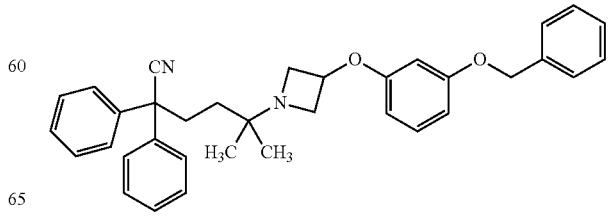

with ethyl acetate and activated charcoal to form a mixture, filtering, adding acetic acid and subjecting the mixture to catalytic hydrogenation, washing with sodium hydroxide and adding toluene and benzoic acid to form the compound of formula I

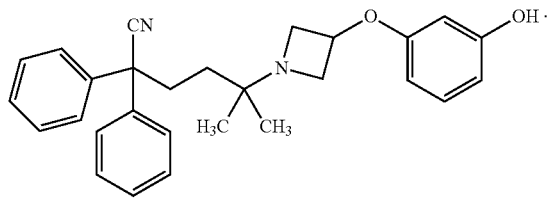

The benzoate compound of formula I can be subsequently used to prepare the crude carboxamide hydrochloride of formula II

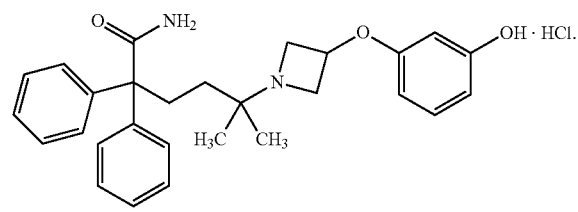

-continued

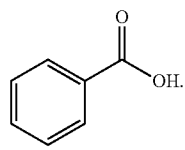

Once formed, the crude carboxamide hydrochloride of formula II can be purified as illustrated in Reaction Scheme 2 above. Thereafter, in some embodiments, in order to prepare the purified carboxamide hydrochloride of formula II for administration via an inhalation route, the resulting non-micronized purified carboxamide hydrochloride can be subjected to micronization to a size suitable for delivery by inhalation (typically less than 5 microns) using techniques available to one of ordinary skill in the art, for example, comminuting techniques, such as spiral jet milling, fluid bed jet milling, supercritical fluid processing to form nanoparticles, high pressure homogenisation, or spray drying as illustrated in the Scheme 11 below:

Scheme 11 - Micronization of Non-micronized Carboxamide Hydrochloride

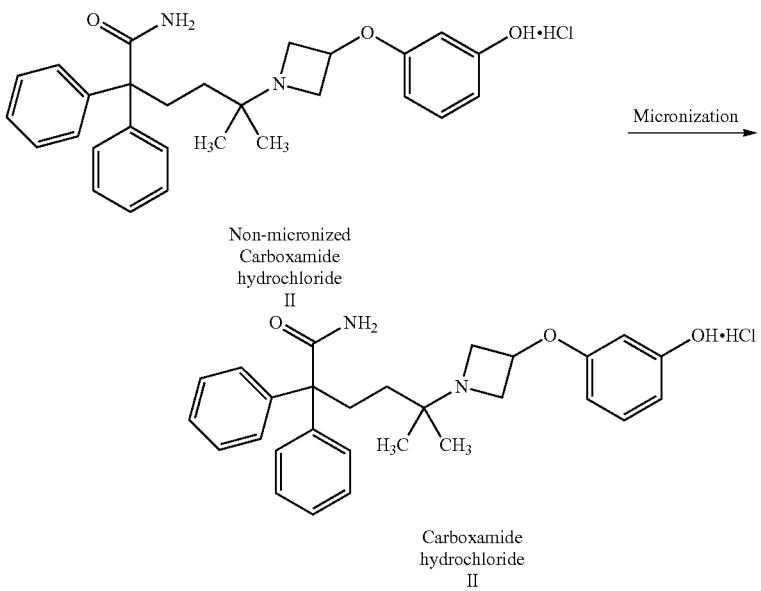

In some embodiments, the particle size of the non-micronized carboxamide compound of this disclosure has a particle size distribution D90 which varies from about 75 micrometers to about 350 micrometers.

Pharmaceutically acceptable salts of the carboxamide and intermediates described in this application include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caproic, caprylic, capric, lauric, mystiric, palmitic, stearic, arachidic or the like.

The term "hydrochloride salt" includes the hydrochloride salt of 5-[3-(3-hydroxyphenoxy)azetidin-1-yl]-5-methyl-2, 2-diphenylhexanamide and its derived forms. The hydrochloride salt of the current application is a valuable pharmaceutically active compound, which is suitable for the therapy and prophylaxis of numerous disorders in which muscarinic receptors are involved or in which antagonism of this receptor may induce benefit, in particular the allergic and non-allergic airways diseases (e.g., asthma, COPD), but also in the treatment of other diseases such as Inflammatory Bowel Disease, Irritable Bowel Disease, diverticular disease, motion sickness, gastric ulcers, radiological examination of the bowel, symptomatic treatment of BPH (benign prostatic hyperplasia), NSAID induced gastric ulceration, urinary incontinence (including urgency, frequency, urge incontinence, overactive bladder, nocturia and lower urinary tract symptoms), cycloplegia, mydriatics and Parkinson's disease.

The hydrochloride salt of the current application can be administered according to the current application to animals, preferably to mammals, and in particular to humans, as pharmaceutical for therapy and/or prophylaxis.

It has been found that the hydrochloride salt of this application is an antagonist of the $M_3$ receptor that is particularly useful for the treatment of $M_3$-mediated diseases and/or conditions, and shows good potency, in particular when administered via the inhalation route. The hydrochloride salt of the current application is particularly suitable for an administration by the inhalation route.

In various embodiments, the carboxamide compound may be present in amorphous, crystalline or semicrystalline form; where the crystalline form may include polymorphs, solvates or hydrates.

In the foregoing and in the following examples, all temperatures are set forth in Celsius degrees; and, unless otherwise indicated, all parts and percentages are by weight. These and other aspects of the present application will be further appreciated upon consideration of the following Examples, which are intended to illustrate certain particular embodiments of the application but are not intended to limit its scope, as defined by the claims.

EXAMPLES

Example 1: Preparation of
5-methyl-2,2-diphenylhex-5-enenitrile (diphenyl alkene)

To a stirred solution of 3-methyl-3-buten-1-ol (100 gm), toluene (1000 ml) and triethylamine (141 gm) at 0-5° C., methanesulfonyl chloride (146.3 gm) at about 15° C. was added and the reaction mass stirred for 60 minutes. To the above reaction mass, 1.0% HCl (500 ml) at room temperature (RT) was added and the resulting mixture stirred for 15-20 minutes, the organic layer was separated and washed with water (500 ml), and then washed with 10% brine solution (500 ml). To the above toluene solution, diphenylacetonitrile (230 gm), tetrabutylammonium bromide (TBAB) (73 gm) and a solution of sodium hydroxide water (226.5 g in 197 ml) was added and stirred at 103-111° C. Water was collected through azeotrope, and upon complete conversion, water (1400 ml) was added and stirred. The organic layer was separated, further washed with 0.5% HCl (745 ml), and then the organic layer was distilled completely and co-distilled with isopropyl alcohol (100 ml). To the above residue, isopropyl alcohol (370 ml) and water (185 ml) were added and the mixture stirred for a period of 30 minutes. A thick slurry was formed which was filtrated followed by washing with isopropyl alcohol (IPA):water (1:1 ratio) (370 ml×2). The product was then dried in a vacuum to produce 5-methyl-2,2-diphenylhex-5-enenitrile (diphenyl alkene). The product was in an amount of about 260 grams (85%) as an off white solid.

Example 2: Preparation of 2-chloro-N-(5-cyano-2-methyl-5,5-diphenylpentan-2-yl)acetamide (diphenyl chloroamide)

To diphenyl alkene (100 gm), chloroacetonitrile (43.3 gm) and acetic acid (91.3 gm) at 0-5° C., sulphuric acid (59.6 gm) was slowly added maintaining the temperature between 0-5° C. The reaction mass was stirred at RT for 2-3 hours. Upon complete conversion, water (600 ml) was added slowly to the reaction mass, the resulting suspension was filtered and the wet cake washed with water (200 ml). The product was then dried in an oven to produce 2-chloro-N-(5-cyano-2-methyl-5,5-diphenylpentan-2-yl)acetamide (diphenyl chloroamide). The product was in an amount of about 63 grams at (46%) as an off white solid.

Example 3: Preparation of
5-amino-5-methyl-2,2-diphenylhexanenitrile
(diphenyl amine)

To diphenyl chloroamide (100 gm), isopropyl alcohol (1000 ml) and acetic acid (158 gm), thiourea (27.9 gm) was added and the resulting mixture stirred at 80-88° C. for 9 hours. Upon completion of the reaction, isopropyl alcohol was distilled and co-distilled with toluene (100 ml). To the resulting residue, toluene (1000 ml) was added and the mixture stirred to give a solution that was washed with a solution of sodium hydroxide in water (135 g in 1700 ml) in two portions (1250 ml then 450 ml). The resulting organic layer was extracted with a solution of acetic acid in water (350 g in 1050 ml) in four portions (400 ml×3 and 200 ml×1). The combined aqueous layers were washed with toluene (200 ml) and the pH adjusted with 20% sodium hydroxide solution to between 12 to 13. The aqueous layer was extracted with toluene (1000 ml×1 and 500 ml×2) and the combined toluene extraction layers distilled completely. The product was co-distilled with cyclohexane (100 ml), and to the obtained residue, cyclohexane (300 ml) was added and stirred for 60 minutes at 5-10° C. The product was then filtered and dried in a vacuum at 50-60° C. to produce 5-amino-5-methyl-2,2-diphenylhexanenitrile (diphenyl amine) in amount of about 63 gm (80%) as an off white solid.

Example 4: Preparation of 5-(3-hydroxyazetidin-1-yl)-5-methyl-2,2-diphenylhexanenitrile (azetidine alcohol)

To diphenyl amine (100 gm) in isopropyl alcohol (1000 ml), epichlorohydrin (66.46 gm) was added at RT, and the resulting mixture heated and stirred for 15 hours at 83-90° C., where upon the reaction was complete with HPLC indicating <5% starting material content. Thereafter, the reaction mass was completely distilled and co-distilled with toluene (150 ml). To the residue, toluene (1000 ml) was added and stirred for dissolution. The resulting organic layer was extracted with a solution of acetic acid in water (350 gm in 1050 ml) in four portions (400 ml×3 and 200 ml×1). The combined extracted aqueous layers was washed with toluene (150 ml) and the pH of the solution adjusted to 12 to 13 with 20% sodium hydroxide. The aqueous solution was extracted with toluene (1000 ml×1 and 400 ml×2), the combined toluene extraction layers were distilled completely and fresh toluene (100 ml) was added and stirred for dissolution. Heptane (250 ml) was added slowly and the mixture was stirred for 60 minutes. The resulting suspension was filtered and the cake washed with heptane (100 ml). The material was then dried in a vacuum to give 5-(3-hydroxyazetidin-1-yl)-5-methyl-2,2-diphenylhexanenitrile in an amount of about 100 grams (83%) as an off white solid.

Example 5: Preparation of azetidinemesyl hydrochloride (1-(5-cyano-2-methyl-5,5-diphenylpentan-2-yl)azetidin-3-yl methanesulfonate hydrochloride)

To azetidine alcohol (100 gm), toluene (1000 ml) and triethylamine (39.3 gm) at −5° C., a solution of methanesulfonyl chloride in toluene (41.1 gm in 100 ml) was added slowly maintaining the temperature between −5 and 5° C. The resulting mixture was stirred for 1-2 hours between −5 and 5° C. Upon complete conversion, water (500 ml) was added at 0° C.-10° C. and the resultant mixture stirred for 30 minutes at RT. The separated organic layer was treated with sodium sulfate (10 gm). To the dried organic layer (87.3 gm) HCl in IPA (a 15-25% w/w solution, an amount equivalent to 87.3 g based on 15% w/w assay) was added and the suspension stirred for 3-4 hours before the resulting solid was isolated by filtration. The wet cake obtained was washed with hexanes (200 ml) and then dried at 50-55° C. to give azetidinemesyl hydrochloride in an amount of about 120 gm (89%).

Side Chain 3-(Benzyloxy)Phenol (Benzyl Resorcinol)

To resorcinol (125 g), dimethyl formamide (1000 ml) and potassium carbonate (163.5 g), benzyl chloride (100 gm) was added at RT and the resulting mixture heated and stirred for 18 hours at 75-85° C. Upon complete conversion, water (1000 ml) was added, the mixture stirred for 30 minutes, the salts filtered off and washed with toluene (1000 ml). The aqueous layer from filtrate was then separated and extracted with toluene (500 ml), the mixed organic layers were washed with water (500 ml×3), and the organic layer was extracted with 10% aqueous sodium hydroxide solution (500 ml×3). The combined aqueous extracts were adjusted to a pH of 2-3 with concentrated HCl. The resulting aqueous solution was extracted with toluene (500 ml×3) and distilled completely. Toluene (50 ml) and hexanes (300 ml) were added to the residue. The suspension was filtered and washed with hexanes (200 ml) and dried in a vacuum at 30-35° C. to give 3-(benzyloxy)phenol (benzyl resorcinol) in an amount of about 64 g (40%).

Example 6: Preparation of 5-(3-[3-(benzyloxy)phenoxy]azetidine-1-yl)-5-methyl-2,2-diphenylhexanenitrile (benzyl coupled compound)

Azetidine mesyl hydrochloride (100 gm), acetonitrile (1000 ml) and caesium carbonate (145.2 gm) were stirred at RT for 30-90 minutes. Benzyl resorcinol (48.82 gm) was added, the resulting mixture heated and stirred at 75-80° C. for 12 hours. The reaction mass was cooled to RT, the salts were filtered off and washed with acetonitrile. The obtained filtrate was distilled off completely at below 60° C. under a vacuum, and acetonitrile (150 ml) was added and stirred for dissolution. Aqueous sodium hydroxide solution (10 g in 450 mL) was added, and the resulting solid filtrated. The wet cake formed was washed with water (100 ml) and dried at 50-55° C. The resulting material was then slurried with ethyl acetate:hexanes (25 ml:975 ml) at 0-5° C. for 1.5-2 hours. After filtration, the wet cake was washed with hexanes (200 ml) and dried under a vacuum at 50-55° C. to give a benzyl coupled compound in an amount of about 100 gm (87%).

Example 7: Preparation of 5-[3-(3-hydroxyphenoxy)azetidine-1-yl]-5-methyl-2,2-diphenyl hexane nitrile benzoate (coupled compound benzoate)

The benzyl coupled compound (100 g) was treated with PS-133 charcoal (10.0 gm) in ethyl acetate (1000 ml) and filtered through hiflo. The obtained filtrate was then transferred to a hydrogenator. Acetic acid was added along with 10% palladium carbon (type 490) and was stirred under hydrogen at 5-6 kg/cm$^2$ for 12 hours. Once the reaction was completed, Pd/C was filtered, the filtrate washed with 10% sodium hydroxide solution (1000 ml), water (500 ml) and 10% brine (500 ml). The organic layer was distilled completely and co-distilled with toluene (100 ml). Toluene (600 ml) and benzoic acid (about 25 g) was added to the residue and the mixture stirred for 15-20 minutes at 100-110° C., cooled to 55-65° C. and stirred for 60 minutes. The preparation was further cooled to RT and stirred for 5-6 hours followed by filtration. The wet cake was washed with toluene (100 ml) and then the material was dried at 50-60° C. to give 5-[3-(3-hydroxyphenoxy)azetidine-1-yl]-5-methyl-2,2-diphenyl hexane nitrile benzoate (coupled compound benzoate) in an amount of about 90 gm (85%).

Example 8: Preparation of crude 5-[3-(3-hydroxyphenoxy)azetidin-1-yl]-5-methyl-2,2 diphenyl-hexanamide hydrochloride To the coupled compound benzoate (100 g) and tert-amyl alcohol (1000 ml), potassium hydroxide flakes (189.2 gm) was added and argon bubbling was applied for 60 minutes at RT. The temperature was raised to 80-90° C. and maintained for 3 hours. The temperature was further raised to 101-105° C. and maintained for 30 hours. Once the reaction was complete, the reaction mass was cooled and water was added slowly at 50-60° C. and stirred for 30 minutes. The separated organic layer was washed with 15% brine (1000 ml) and the organic layer was adjusted to a pH of 6.5-8.0 with 20% HCl solution. Tert amyl alcohol (200 ml) was added to the separated organic layer and it was distilled to 2 volumes under a vacuum to obtain a water content of between 5% and 10%. The preparation was cooled and concentrated HCl (20.0 g) was added to the reaction mass.

The preparation was stirred at 45-55° C. for 3 hours followed by the addition of a seed material (0.5 gm). The preparation was stirred again for 9-10 hours. The reaction mass was cooled to 20-25° C., stirred for 2 hours, filtered and washed with methyl tert-butyl ether. The resulting sold was slurried in methyl tert-butyl ether (MTBE) (1000 ml), filtered and washed with MTBE (300 ml). The material was then dried under a vacuum at 60-70° C. to give crude 5-[3-(3-hydroxyphenoxy)azetidin-1-yl]-5-methyl-2,2 diphenylhexanamide hydrochloride in an amount of about 75 gm (86%).

Example 9: Purification of 5-[3-(3-hydroxyphenoxy)azetidin-1-yl]-5-methyl-2,2-diphenylhexanamide hydrochloride To the crude 5-[3-(3-hydroxyphenoxy)azetidin-1-yl]-5-methyl-2,2-diphenylhexanamide hydrochloride crude (100 g), IPA (665 ml) and water (285 ml), PF511 SPL carbon (5.0 g) was added and the mixture stirred at 75-85° C. for 15 minutes. The preparation was then filtrated through a hiflo bed and washed with IPA water (7:3 ratio) (100 ml). The preparation was cooled slowly to 60° C., seed material of 5-[3-(3-hydroxyphenoxy)azetidin-1-yl]-5-methyl-2,2-diphenylhexanamide hydrochloride (1.5 g) was added and the mixture stirred for 5 hours. The preparation was further cooled to 50° C., 40° C., 30° C., 20° C., and 10° C. The preparation was stirred for 3 hours at all of the temperatures. The product was filtered and washed with IPA (150 ml). The cake was then dried under a vacuum at 60-70° C., giving purified 5-[3-(3-hydroxyphenoxy)azetidin-1-yl]-5-methyl-2,2-diphenylhexanamide hydrochloride in an amount of about 75 gm (75%).

Example 10: Micronization of 5-[3-(3-hydroxyphenoxy)azetidin-1-yl]-5-methyl-2,2-diphenylhexanamide hydrochloride The purified non-micronized 5-[3-(3-hydroxyphenoxy)azetidin-1-yl]-5-methyl-2,2-diphenylhexanamide hydrochloride of Example 9 can be micronized by jet milling.

Example 11: Hydrolysis of the Nitrile of Formula I to the Corresponding Amide of Formula II A three-necked round bottom flask (RBF) was stirred with a magnetic stirrer, and the temperature monitored via a thermometer. An N2 bubbler and a condenser was also used. Formula I (1 g of Limiting Reagent, 100 equivalence, 18 mmoles, 100 g [Actual]), t-amyl alcohol (amylene hydrate 10 mL/g-bulk-LR, 914 mmoles, 10.000 mL [Actual]), and potassium hydroxide (18.5 equivalent (molar), 18.50 equivalent, 33.7 mmoles, 1.89 g [Actual]) was added to the RBF. The mixture was heated to 85° C. and held at this temperature for 2.5 hours. The reaction temperature was increased to reflux (~104° C.) O/N. Reaction progress was monitored by LCMS (ultra neutral; 215-235 nm). A sample preparation was made out of 1 drop reaction mixture diluted into ~1.5 ml 1:1 MeCN/H$_2$O.

00704919-020-IPC1 (2.5 hours at 85° C., 2.5 hours at reflux): RT at 2.70 minutes (56%) M+H 445 PRODUCT; RT 3.40 minutes (44%) M+H 427 S.M.

00704919-020-IPC2 (2.5 hours at 85° C., 5 hours at reflux): RT 2.66 minutes (79%) M+H 445 PRODUCT; RT 3.38 minutes (21%) M+H 427 S.M.

00704919-020-IPC3 (2.5 hours at 85° C., O/N at reflux): RT 2.71 minutes (100%) M+H 445 PRODUCT.

The mixture became a thick white slurry and significant thickening of the mixture was observed between 4-5 hours reflux. The mixture was allowed to cool to ambient temperature. Water was added and the resultant biphasic solution was stirred for 5 minutes. The phases were separated (aqueous phase, pH 11+ by paper, volume 8.5 ml). Water was charged to the organic phase, followed by hydrogen chloride (PH adjustment) (1.05 equivalence (molar); 19 mmoles; 164.369 µL; [Actual]) to adjust the pH of the aqueous phase to 7 (target range pH 6.5-8; actual pH 7). The phases were separated (aqueous phase, pH 7 by paper, volume 10.5 ml). The organic phase was charged to a clean, dry RBF for crystallization. Hydrogen chloride (salt formation) (1.05 equivalence (molar); 19 mmoles; 164.369 µL; [Actual]) was added, followed by a seed of 5-[3-(3-Hydroxyphenoxy)azetidin-1-yl]-5-methyl-2,2-diphenylhexanamide hydrochloride. Crystallization was observed between 1-3 hours at ambient temperature.

The solid was granulated at ambient temperature for 1 hour, (granulation typically is about 12 hours at ambient temperature) and was isolated. The granulated solid was then washed with tBME (8 ml) and dried over the weekend (4 days) in a vacuum (40° C.). The result was an isolated solid having a dry weight of 0.57 g and a yield of 70%. The yield was lower than the standard reaction, but this is accounted for by the decreased granulation time of 1 hour verse the standard 12-18 hours. Hydrolysis proceeded to completion, indicating that use of Formula I as the benzoic acid salt has no detrimental impact on the reaction.

It will be apparent to those of ordinary skill in the art that various modifications and variations can be made to various embodiments described herein without departing from the spirit or scope of the teachings herein. Thus, it is intended that various embodiments cover other modifications and variations of various embodiments within the scope of the present teachings.

The invention claimed is:

1. A method for preparing a carboxamide compound, the method comprising reacting 5-[3-(3-hydroxyphenoxy)azetidin-1-yl]-5-methyl-2,2-diphenylhexanenitrile benzoate with a reagent and hydrochloric acid to form the carboxamide compound comprising 5-[3-(3-hydroxyphenoxy)azetidin-1-yl]-5-methyl-2,2-diphenylhexanamide hydrochloride.

2. The method of claim 1, wherein the reagent comprises a base and an alcohol.

3. The method of claim 2, wherein the base comprises potassium hydroxide and the alcohol comprises a tertiary amyl alcohol.

4. The method of claim 2, further comprising washing the 5-[3-(3-hydroxyphenoxy)azetidin-1-yl]-5-methyl-2,2-diphenylhexanamide hydrochloride with a mixture comprising an alcohol and an ether.

5. The method of claim 4, wherein the alcohol of the mixture comprises tertiary amyl alcohol and the ether of the mixture comprises methyl tert-butyl ether.

6. The method of claim 1, wherein the 5-[3-(3-hydroxyphenoxy)azetidin-1-yl]-5-methyl-2,2-diphenylhexanenitrile benzoate is prepared by reacting a benzyl coupled compound comprising 5-(3-(3-(benzyloxy)phenoxy)azetidin-1-yl)-5-methyl-2,2-diphenylhexanenitrile with ethyl acetate and/or acetic acid and activated charcoal to form a mixture, filtering and subjecting the resulting mixture to catalytic hydrogenation, washing with sodium hydroxide and adding toluene and benzoic acid to the mixture to form the 5-[3-(3-hydroxyphenoxy)azetidin-1-yl]-5-methyl-2,2-diphenylhexanenitrile benzoate.

7. The method of claim 6, wherein the benzyl coupled compound is prepared by reacting an azetidine mesyl HCl comprising 1-(5-cyano-2-methyl-5,5-diphenylpentan-2-yl)azetidin-3-yl methanesulfonate hydrochloride with a reagent comprising benzyl resorcinol.

8. The method of claim 7, wherein: (i) the reagent further comprises acetonitrile and cesium carbonate or potassium carbonate; (ii) the benzyl resorcinol is prepared by reacting resorcinol with benzyl chloride to form benzyl resorcinol; or (iii) the benzyl resorcinol is prepared by reacting resorcinol with benzyl chloride, potassium carbonate and dimethylformamide.

9. The method of claim 7, wherein: (i) the azetidine mesyl HCl is prepared by reacting azetidine alcohol with methanesulfonyl chloride; or (ii) the azetidine mesyl HCl is prepared by reacting azetidine alcohol with methanesulfonyl chloride, triethylamine, HCl in isopropyl alcohol and toluene.

10. The method of claim 9, wherein: (i) the azetidine alcohol is prepared by reacting a diphenyl amine with epichlorohydrin; or (ii) the azetidine alcohol is prepared by reacting a diphenyl amine with epichlorohydrin, isopropyl alcohol, acetic acid, toluene and heptane.

11. The method of claim 10, wherein: (i) the diphenyl amine is prepared by reacting diphenyl chloro amide with thiourea; or (ii) the diphenyl amine is prepared by reacting diphenyl chloro amide with thiourea, acetic acid and isopropyl alcohol.

12. The method of claim 11, wherein: (i) the diphenyl chloro amide is prepared by reacting a diphenyl alkene with chloroacetonitrile; or (ii) the diphenyl chloro amide is prepared by reacting a diphenyl alkene with chloroacetonitrile, acetic acid and sulfuric acid.

13. The method of claim 12, wherein: (i) the diphenyl alkene is prepared by reacting 3-methyl-3-buten-1-ol with methanesulfonyl chloride and diphenylacetonitrile; (ii) the diphenyl alkene is prepared by reacting 3-methyl-3-buten-1-ol with methanesulfonyl chloride to form a mesyl alkene intermediate, and treating the mesyl alkene intermediate with diphenylacetonitrile, tetrabutyl ammonium bromide and sodium hydroxide; or (iii) the diphenyl alkene is prepared by reacting 3-methyl-3-buten-1-ol with methanesulfonyl chloride to form a mesyl alkene intermediate, and treating the mesyl alkene intermediate with diphenylacetonitrile, tetrabutyl ammonium bromide and sodium hydroxide, toluene and triethylamine.

14. A method for preparing a carboxamide compound, the method comprising the steps of:
 (i) reacting 3-methyl-3-buten-1-ol with methanesulfonyl chloride and diphenylacetonitrile to form a diphenyl alkene;
 (ii) reacting the diphenyl alkene with chloroacetonitrile to form a diphenyl chloro amide;
 (iii) reacting the diphenyl chloro amide with thiourea to form a diphenyl amine;
 (iv) reacting the diphenyl amine with epichlorohydrin to form azetidine alcohol;
 (v) reacting the azeditine alcohol with methanesulfonyl chloride to form azetidine mesyl HCl;
 (vi) reacting the azetidine mesyl HCl with benzyl resorcinol to form a benzyl coupled compound;
 (vii) reacting the benzyl coupled compound with ethyl acetate and/or acetic acid and filtering to form a mixture;
 (viii) subjecting the mixture to catalytic hydrogenation;
 (ix) adding sodium hydroxide, toluene and benzoic acid to the mixture in step (viii) to form 5-[3-(3-hydroxyphenoxy)azetidin-1-yl]-5-methyl-2,2-diphenylhexanenitrile benzoate; and
 (x) reacting 5-[3-(3-hydroxyphenoxy)azetidin-1-yl]-5-methyl-2,2-diphenylhexanenitrile benzoate with a reagent and hydrochloric acid to form 5-[3-(3-hydroxyphenoxy)azetidin-1-yl]-5-methyl-2,2-diphenylhexanamide hydrochloride.

15. A method for preparing a coupled compound benzoate of formula I

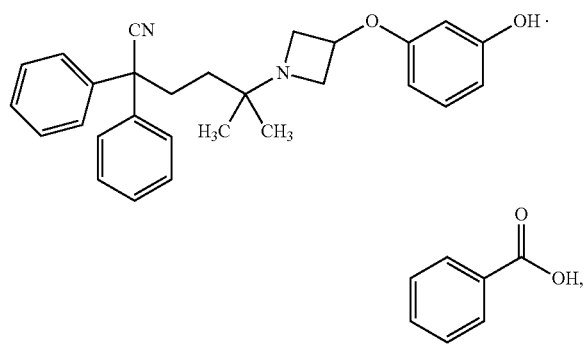

the method comprising reacting a benzyl coupled compound of formula III

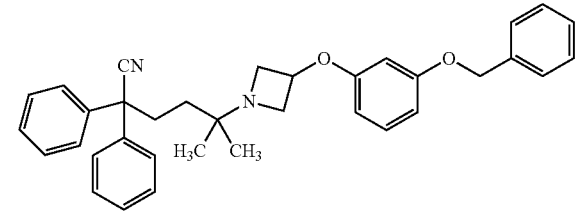 [SMILES: CC(C)(CCC(C#N)(c1ccccc1)c1ccccc1)N1CC(Oc2cccc(OCc3ccccc3)c2)C1]

with ethyl acetate and/or acetic acid and activated charcoal and filtering to form a mixture, subjecting the mixture to catalytic hydrogenation and adding sodium hydroxide, toluene and benzoic acid to the mixture to form the compound of formula I

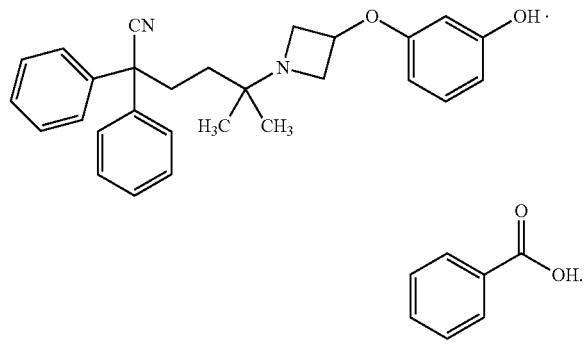

16. The method of claim 1, wherein the carboxamide compound comprising 5-[3-(3-hydroxyphenoxy)azetidin-1-yl]-5-methyl-2,2-diphenylhexanamide hydrochloride is micronized.

17. The method of claim 1, wherein the carboxamide compound has a particle size distribution D90 in the range of from about 75 micrometers to about 350 micrometers.

* * * * *